US012661390B2

(12) United States Patent
Wagner et al.

(10) Patent No.: US 12,661,390 B2
(45) Date of Patent: Jun. 23, 2026

(54) ADAMTS13 TREATMENT TO ENHANCE GRAFT SURVIVAL

(71) Applicant: THE CHILDREN'S MEDICAL CENTER CORPORATION, Boston, MA (US)

(72) Inventors: Denisa D. Wagner, Dover, MA (US); Siu Ling Wong, Singapore (SG)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 638 days.

(21) Appl. No.: 17/765,728

(22) PCT Filed: Oct. 2, 2020

(86) PCT No.: PCT/US2020/053901
§ 371 (c)(1),
(2) Date: Mar. 31, 2022

(87) PCT Pub. No.: WO2021/067668
PCT Pub. Date: Apr. 8, 2021

(65) Prior Publication Data
US 2022/0339266 A1 Oct. 27, 2022

Related U.S. Application Data

(60) Provisional application No. 62/911,019, filed on Oct. 4, 2019.

(51) Int. Cl.
*A61K 38/48* (2006.01)
*A61K 45/06* (2006.01)
*A61P 37/06* (2006.01)

(52) U.S. Cl.
CPC .......... *A61K 38/4886* (2013.01); *A61K 45/06* (2013.01); *A61P 37/06* (2018.01); *C12Y 304/24082* (2013.01)

(58) Field of Classification Search
CPC ........................... A61K 38/4886; A61P 37/06
See application file for complete search history.

(56) References Cited

U.S. PATENT DOCUMENTS

| | | | |
|---|---|---|---|
| 8,623,352 B2 | 1/2014 | Mathiessen et al. | |
| 8,945,895 B2 | 2/2015 | Hasslacher et al. | |
| 11,567,080 B2 | 1/2023 | Hata et al. | |
| 2005/0266528 A1 | 12/2005 | Laemmie et al. | |
| 2011/0086413 A1 | 4/2011 | Grillberger et al. | |
| 2011/0229455 A1 | 9/2011 | Mathiessen et al. | |
| 2013/0136732 A1* | 5/2013 | Wagner | C12N 9/6489 424/94.67 |
| 2014/0271611 A1 | 9/2014 | Schiviz et al. | |
| 2017/0196945 A1* | 7/2017 | Wagner | A61K 38/49 |
| 2019/0161746 A1 | 5/2019 | Wagner et al. | |

FOREIGN PATENT DOCUMENTS

| | | |
|---|---|---|
| JP | 2010-280571 A | 12/2010 |
| WO | 2002042441 A2 | 5/2002 |
| WO | 2012006594 A1 | 1/2012 |
| WO | 2014151968 A1 | 9/2014 |
| WO | 2017/119498 A1 | 7/2017 |

OTHER PUBLICATIONS

Mangold et al., "Coronary Neutrophil Extracellular Trap Burden and Deoxyribonuclease Activity in ST-Elevation Acute Coronary Syndrome Are Predictors of ST-Segment Resolution and Infarct Size", Circulation Research, vol. 116, No. 7, p. 1182-1192. (Year: 2015).*
Rahmel, "Vascularized Composite Allografts: Procurement, Allocation, and Implementation", Current Transplantation Reports, vol. 1, pp. 173-182. (Year: 2014).*
Motsch et al., "Microvascular integrity plays an important role for graft survival after experimental skin transplantation", Transplant Immunology, vol. 33, pp. 204-209. (Year: 2015).*
Hugenholtz et al. "An unbalance between von Willebrand factor and ADAMTS13 in acute liver failure: Implications for hemostasis and clinical outcome", Hepatology 58.2: 752-761 (2013).
Ko et al. "Plasma ADAMTS13 activity may predict early adverse events in living donor liver transplantation: Observations in 3 cases", Liver Transplantation 12.5: 859-869 (2006).
Kobayashi et al. "Decreased ADAMTS13 Levels in Patients after Living Donor Liver Transplantation", Thrombosis Research 124.5: 541-545 (2009).
Matsui et al. "ADAMTS13 Improving the Cell Engraftment Efficacy in Mouse Model of Bone Marrow Transplantation", Blood 120.21: Abstract 1077 (2012).
Benichou et al. "Immune recognition and rejection of allogeneic skin grafts." Immunotherapy 3(6) 757-770 (2011).
Chauhan et al. "ADAMTS13: a new link between thrombosis and inflammation." The Journal of experimental medicine 205(9): 2065-2074 (2008).
Chen et al. "Inflammation, von Willebrand factor, and ADAMTS13." Blood 132(2): 141-147 (2018).
Cheng et al. "Murine full-thickness skin transplantation." JoVE (Journal of Visualized Experiments) (119): e55105 (2017).

(Continued)

*Primary Examiner* — Melenie L Gordon
*Assistant Examiner* — Grant C Currens
(74) *Attorney, Agent, or Firm* — Nixon Peabody LLP; David S. Resnick; Nicole D. Kling

(57) ABSTRACT

The disclosure provides a method for treating and/or preventing graft rejection with A Disintegrin And Metalloproteinase with Thrombospondin type 1 motif, member-13 (ADAMT S13). The disclosure provides a method for increasing ADAMTS13-mediated von Willebrand factor (VWF) cleavage in a subject that received a graft by administering ADAMTS13. The disclosure also provides a method of determining the likelihood that a subject will rejection a graft.

18 Claims, 6 Drawing Sheets

Specification includes a Sequence Listing.

(56) References Cited

OTHER PUBLICATIONS

Emil et al. "Hemolytic uremic syndrome in a child with burn injuries." The Journal of burn care & rehabilitation 19(2): 135-137 (1998).

Fuchs et al. "Extracellular DNA traps promote thrombosis." PNAS107(36): 15880-15885 (2010).

Gelman et al. "Cutting edge: Acute lung allograft rejection is independent of secondary lymphoid organs." The Journal of Immunology 182(7): 3969-3973 (2009).

Grassle et al. "von Willebrand factor directly interacts with DNA from neutrophil extracellular traps." Arteriosclerosis, thrombosis, and vascular biology 34(7): 1382-1389 (2014).

Han et al. "A shear-based assay for assessing plasma ADAMTS13 activity and inhibitors in patients with thrombotic thrombocytopenia purpura." Transfusion 51(7): 1580-1591 (2011).

Johnson et al. "Combat-related facial burns: analysis of strategic pitfalls." Journal of Oral and Maxillofacial Surgery 73(1): 106-111 (2015).

Kanitakis et al. "Capillary thrombosis in the skin: a pathologic hallmark of severe/chronic rejection of human vascularized composite tissue allografts?" Transplantation 100(4): 954-957 (2016).

Kariya et al., "Direct evidence for activated CD8+ T cell transmigration across portal vein endothelial cells in liver graft rejection." Journal of gastroenterology 51(10): 985-998 (2016).

Kawecki et al. "von Willebrand factor and inflammation." Journal of Thrombosis and Haemostasis 15(7) 1285-1294 (2017).

Kitala et al., "Allogeneic vs. Autologous Skin Grafts in the Therapy of Patients with Burn Injuries: A Retrospective, Open-label Clinical Study with Pair Matching." Adv Clin Exp Med. 25(5): 923-929 (2016).

Kiuchi et al. "Background and Prognostic Implications of Perireperfusion Tissue Injuries in Human Liver Transplants: A Panel Histochemical Study." Transplantation 66(6): 737-747 (1998).

Kokame et al. "VWF73, a region from D1596 to R1668 of von Willebrand factor, provides a minimal substrate for ADAMTS-13." Blood 103(2): 607-612 (2004).

Kokame et al. "FRETS-VWF73, a first fluorogenic substrate for ADAMTS13 assay." British journal of haematology 129(1): 93-100 (2005).

Landsman et al. "Characterization of a cryopreserved split-thickness human skin allograft—TheraSkin." Advances in skin & wound care 29(9): 399-406 (2016).

Lewis et al. "Inhibition of PAD4 activity is sufficient to disrupt mouse and human NET formation." Nature chemical biology 11(3): 189-191 (2015).

Li et al. "PAD4 is essential for antibacterial innate immunity mediated by neutrophil extracellular traps." Journal of Experimental Medicine 207(9): 1853-1862 (2010).

Maile et al. "Lymphopenia-induced homeostatic proliferation of CD8+ T cells is a mechanism for effective allogeneic skin graft rejection following burn injury." The Journal of Immunology 176(11): 6717-6726 (2006).

Mishra et al. "Cutting edge: protein arginine deiminase 2 and 4 regulate NLRP3 inflammasome-dependent IL-1β maturation and ASC speck formation in macrophages." The Journal of Immunology 203(4): 795-800 (Jul. 2019).

Moake. "Thrombotic microangiopathies." New England Journal of Medicine 347(8): 589-600 (2002).

Münzer et al. "Abstract 118: Assembly of the Nlrp3 inflammasome regulates NET formation and is promoted by the vimentin intermediate filament cytoskeletal system." Arteriosclerosis, Thrombosis, and Vascular Biology 39(Suppl_1): A118 (Jul. 2019).

Nolasco et al. "Hemolytic uremic syndrome—associated Shiga toxins promote endothelial-cell secretion and impair ADAMTS13 cleavage of unusually large von Willebrand factor multimers." Blood 106(13): 4199-4209 (2005).

Otawara et al. "Microfluidic assay measures increased neutrophil extracellular traps circulating in blood after burn injuries." Scientific Reports 8(1): 1-9 (2018).

Öztürk et al. "Can burn injury cause thrombotic thrombocytopenia purpura?" Southern Clinics of Istanbul Eurasia 30(2) 175-177 (2019).

Peyvandi et al. "ADAMTS-13 assays in thrombotic thrombocytopeniarpura." Journal of Thrombosis and Haemostasis 8(4): (2010): 631-640 (2010).

Pilon et al. "Administration of low doses of IL-2 combined to rapamycin promotes allogeneic skin graft survival in mice." American Journal of Transplantation 14(12): 2874-2882 (2014).

Plaimauer et al., "Cloning, expression, and functional characterization of the von Willebrand factor-cleaving protease (ADAMTS13)." Blood 100(10): 3626-32 (2002).

Plaimauer et al. "Expression and characterization of recombinant human ADAMTS-13." Seminars in hematology 41(1): 24-33 (2004).

Rieger et al. "Relation between ADAMTS13 activity and ADAMTS13 antigen levels in healthy donors and patients with thrombotic microangiopathies (TMA)." Thrombosis and haemostasis 95(02): 212-220 (2006).

Saffarzadeh et al. "Neutrophil extracellular traps directly induce epithelial and endothelial cell death: A predominant role of histones." PloS one 7(2): 1-14 (2012).

Sayah et al. "Neutrophil extracellular traps are pathogenic in primary graft dysfunction after lung transplantation." American journal of respiratory and critical care medicine 191(4): 455-463 (2015).

Scozzi et al. "Neutrophil extracellular trap fragments stimulate innate immune responses that prevent lung transplant tolerance." American Journal of Transplantation 19(4): 1011-1023 (Apr. 2019).

Scully et al. "Recombinant ADAMTS-13: first-in-human pharmacokinetics and safety in congenital thrombotic thrombocytopenia purpura." Blood 130(19): 2055-2063 (2017).

Shim et al. "Platelet-VWF complexes are preferred substrates of ADAMTS13 under fluid shear stress." Blood 111(2): 651-657 (2008).

Sorvillo et al. "Plasma peptidylarginine deiminase IV promotes VWF-platelet string formation and accelerates thrombosis after vessel injury." Circulation research 125(5): 507-519 (Aug. 2019).

Sun et al. "Citrullination of NF-κB p65 promotes its nuclear localization and TLR-induced expression of IL-1β and TNFα." Science immunology 2(12): 1-32 (2017).

Suri. "The use of human deoxyribonuclease (rhDNase) in the management of cystic fibrosis." BioDrugs 19(3): 135-144 (2005).

Tillack et al. "T lymphocyte priming by neutrophil extracellular traps links innate and adaptive immune responses." The Journal of Immunology 188(7): 3150-3159 (2012).

Wolf et al. "Comparison between civilian burns and combat burns from Operation Iraqi Freedom and Operation Enduring Freedom." Annals of surgery 243(6): 786-795 (2006).

Wong et al. "Diabetes primes neutrophils to undergo NETosis, which impairs wound healing." Nature medicine 21(7): 815-819 (2015).

Xu et al. "Extracellular histones are major mediators of death in sepsis." Nature medicine 15(11): 1318-1321 (2009).

Hull et al., "Why some organ allografts are tolerated better than others: new insights for an old question." Current opinion in organ transplantation 24.1: 49-57 (2019).

Jansen et al. "Release of extracellular DNA influences renal ischemia reperfusion injury by platelet activation and formation of neutrophil extracellular traps." Kidney international vol. 91,2 (2017): 352-364.

Khodor et al. "Clopidogrel-induced refractory thrombotic thrombocytopenia purpura successfully treated with rituximab." Hematology/oncology and stem cell therapy 9,2 (2016): 76-79.

Savchenko et al. "VWF-mediated leukocyte recruitment with chromatin decondensation by PAD4 increases myocardial ischemia/reperfusion injury in mice." Blood 123.1 : 141-148 (2014).

* cited by examiner

Scale, 50 μm

SEQUENCE LISTING

```
<160> NUMBER OF SEQ ID NOS: 3

<210> SEQ ID NO 1
<211> LENGTH: 1427
<212> TYPE: PRT
<213> ORGANISM: Homo sapiens

<400> SEQUENCE: 1

Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
            20                  25                  30

Phe Gln Gln Ser Cys Leu Gln Ala Leu Glu Pro Gln Ala Val Ser Ser
        35                  40                  45

Tyr Leu Ser Pro Gly Ala Pro Leu Lys Gly Arg Pro Pro Ser Pro Gly
    50                  55                  60

Phe Gln Arg Gln Arg Gln Arg Gln Arg Ala Ala Gly Gly Ile Leu
65                  70                  75                  80

His Leu Glu Leu Leu Val Ala Val Gly Pro Asp Val Phe Gln Ala His
                85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
```

```
145               150               155               160

Ile Asn Pro Glu Asp Asp Thr Asp Pro Gly His Ala Asp Leu Val Leu
              165               170               175

Tyr Ile Thr Arg Phe Asp Leu Glu Leu Pro Asp Gly Asn Arg Gln Val
              180               185               190

Arg Gly Val Thr Gln Leu Gly Gly Ala Cys Ser Pro Thr Trp Ser Cys
              195               200               205

Leu Ile Thr Glu Asp Thr Gly Phe Asp Leu Gly Val Thr Ile Ala His
     210               215               220

Glu Ile Gly His Ser Phe Gly Leu Glu His Asp Gly Ala Pro Gly Ser
225               230               235               240

Gly Cys Gly Pro Ser Gly His Val Met Ala Ser Asp Gly Ala Ala Pro
              245               250               255

Arg Ala Gly Leu Ala Trp Ser Pro Cys Ser Arg Arg Gln Leu Leu Ser
              260               265               270

Leu Leu Ser Ala Gly Arg Ala Arg Cys Val Trp Asp Pro Pro Arg Pro
              275               280               285

Gln Pro Gly Ser Ala Gly His Pro Pro Asp Ala Gln Pro Gly Leu Tyr
     290               295               300

Tyr Ser Ala Asn Glu Gln Cys Arg Val Ala Phe Gly Pro Lys Ala Val
305               310               315               320

Ala Cys Thr Phe Ala Arg Glu His Leu Asp Met Cys Gln Ala Leu Ser
              325               330               335

Cys His Thr Asp Pro Leu Asp Gln Ser Ser Cys Ser Arg Leu Leu Val
              340               345               350

Pro Leu Leu Asp Gly Thr Glu Cys Gly Val Glu Lys Trp Cys Ser Lys
              355               360               365

Gly Arg Cys Arg Ser Leu Val Glu Leu Thr Pro Ile Ala Ala Val His
     370               375               380

Gly Arg Trp Ser Ser Trp Gly Pro Arg Ser Pro Cys Ser Arg Ser Cys
385               390               395               400

Gly Gly Gly Val Val Thr Arg Arg Arg Gln Cys Asn Asn Pro Arg Pro
              405               410               415

Ala Phe Gly Gly Arg Ala Cys Val Gly Ala Asp Leu Gln Ala Glu Met
              420               425               430

Cys Asn Thr Gln Ala Cys Glu Lys Thr Gln Leu Glu Phe Met Ser Gln
              435               440               445

Gln Cys Ala Arg Thr Asp Gly Gln Pro Leu Arg Ser Ser Pro Gly Gly
     450               455               460

Ala Ser Phe Tyr His Trp Gly Ala Ala Val Pro His Ser Gln Gly Asp
465               470               475               480

Ala Leu Cys Arg His Met Cys Arg Ala Ile Gly Glu Ser Phe Ile Met
              485               490               495

Lys Arg Gly Asp Ser Phe Leu Asp Gly Thr Arg Cys Met Pro Ser Gly
              500               505               510

Pro Arg Glu Asp Gly Thr Leu Ser Leu Cys Val Ser Gly Ser Cys Arg
              515               520               525

Thr Phe Gly Cys Asp Gly Arg Met Asp Ser Gln Gln Val Trp Asp Arg
              530               535               540

Cys Gln Val Cys Gly Gly Asp Asn Ser Thr Cys Ser Pro Arg Lys Gly
545               550               555               560

Ser Phe Thr Ala Gly Arg Ala Arg Glu Tyr Val Thr Phe Leu Thr Val
              565               570               575
```

-continued

```
Thr Pro Asn Leu Thr Ser Val Tyr Ile Ala Asn His Arg Pro Leu Phe
        580                 585                 590

Thr His Leu Ala Val Arg Ile Gly Gly Arg Tyr Val Ala Gly Lys
        595                 600                 605

Met Ser Ile Ser Pro Asn Thr Thr Tyr Pro Ser Leu Leu Glu Asp Gly
        610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655

Val Tyr Arg Arg Tyr Gly Glu Glu Tyr Gly Asn Leu Thr Arg Pro Asp
                660                 665                 670

Ile Thr Phe Thr Tyr Phe Gln Pro Lys Pro Arg Gln Ala Trp Val Trp
        675                 680                 685

Ala Ala Val Arg Gly Pro Cys Ser Val Ser Cys Gly Ala Gly Leu Arg
        690                 695                 700

Trp Val Asn Tyr Ser Cys Leu Asp Gln Ala Arg Lys Glu Leu Val Glu
705                 710                 715                 720

Thr Val Gln Cys Gln Gly Ser Gln Gln Pro Pro Ala Trp Pro Glu Ala
                725                 730                 735

Cys Val Leu Glu Pro Cys Pro Pro Tyr Trp Ala Val Gly Asp Phe Gly
                740                 745                 750

Pro Cys Ser Ala Ser Cys Gly Gly Gly Leu Arg Glu Arg Pro Val Arg
        755                 760                 765

Cys Val Glu Ala Gln Gly Ser Leu Leu Lys Thr Leu Pro Pro Ala Arg
        770                 775                 780

Cys Arg Ala Gly Ala Gln Gln Pro Ala Val Ala Leu Glu Thr Cys Asn
785                 790                 795                 800

Pro Gln Pro Cys Pro Ala Arg Trp Glu Val Ser Glu Pro Ser Ser Cys
                805                 810                 815

Thr Ser Ala Gly Gly Ala Gly Leu Ala Leu Glu Asn Glu Thr Cys Val
                820                 825                 830

Pro Gly Ala Asp Gly Leu Glu Ala Pro Val Thr Glu Gly Pro Gly Ser
        835                 840                 845

Val Asp Glu Lys Leu Pro Ala Pro Glu Pro Cys Val Gly Met Ser Cys
850                 855                 860

Pro Pro Gly Trp Gly His Leu Asp Ala Thr Ser Ala Gly Glu Lys Ala
865                 870                 875                 880

Pro Ser Pro Trp Gly Ser Ile Arg Thr Gly Ala Gln Ala Ala His Val
                885                 890                 895

Trp Thr Pro Ala Ala Gly Ser Cys Ser Val Ser Cys Gly Arg Gly Leu
        900                 905                 910

Met Glu Leu Arg Phe Leu Cys Met Asp Ser Ala Leu Arg Val Pro Val
        915                 920                 925

Gln Glu Glu Leu Cys Gly Leu Ala Ser Lys Pro Gly Ser Arg Arg Glu
        930                 935                 940

Val Cys Gln Ala Val Pro Cys Pro Ala Arg Trp Gln Tyr Lys Leu Ala
945                 950                 955                 960

Ala Cys Ser Val Ser Cys Gly Arg Gly Val Val Arg Arg Ile Leu Tyr
                965                 970                 975

Cys Ala Arg Ala His Gly Glu Asp Asp Gly Glu Glu Ile Leu Leu Asp
        980                 985                 990
```

-continued

```
Thr Gln Cys Gln Gly Leu Pro Arg  Pro Glu Pro Gln Glu  Ala Cys Ser
        995              1000             1005

Leu Glu  Pro Cys Pro Pro Arg  Trp Lys Val Met Ser  Leu Gly Pro
    1010             1015             1020

Cys Ser  Ala Ser Cys Gly Leu  Gly Thr Ala Arg Arg  Ser Val Ala
    1025             1030             1035

Cys Val  Gln Leu Asp Gln Gly  Gln Asp Val Glu Val  Asp Glu Ala
    1040             1045             1050

Ala Cys  Ala Ala Leu Val Arg  Pro Glu Ala Ser Val  Pro Cys Leu
    1055             1060             1065

Ile Ala  Asp Cys Thr Tyr Arg  Trp His Val Gly Thr  Trp Met Glu
    1070             1075             1080

Cys Ser  Val Ser Cys Gly Asp  Gly Ile Gln Arg Arg  Arg Asp Thr
    1085             1090             1095

Cys Leu  Gly Pro Gln Ala Gln  Ala Pro Val Pro Ala  Asp Phe Cys
    1100             1105             1110

Gln His  Leu Pro Lys Pro Val  Thr Val Arg Gly Cys  Trp Ala Gly
    1115             1120             1125

Pro Cys  Val Gly Gln Gly Thr  Pro Ser Leu Val Pro  His Glu Glu
    1130             1135             1140

Ala Ala  Ala Pro Gly Arg Thr  Thr Ala Thr Pro Ala  Gly Ala Ser
    1145             1150             1155

Leu Glu  Trp Ser Gln Ala Arg  Gly Leu Leu Phe Ser  Pro Ala Pro
    1160             1165             1170

Gln Pro  Arg Arg Leu Leu Pro  Gly Pro Gln Glu Asn  Ser Val Gln
    1175             1180             1185

Ser Ser  Ala Cys Gly Arg Gln  His Leu Glu Pro Thr  Gly Thr Ile
    1190             1195             1200

Asp Met  Arg Gly Pro Gly Gln  Ala Asp Cys Ala Val  Ala Ile Gly
    1205             1210             1215

Arg Pro  Leu Gly Glu Val Val  Thr Leu Arg Val Leu  Glu Ser Ser
    1220             1225             1230

Leu Asn  Cys Ser Ala Gly Asp  Met Leu Leu Leu Trp  Gly Arg Leu
    1235             1240             1245

Thr Trp  Arg Lys Met Cys Arg  Lys Leu Leu Asp Met  Thr Phe Ser
    1250             1255             1260

Ser Lys  Thr Asn Thr Leu Val  Val Arg Gln Arg Cys  Gly Arg Pro
    1265             1270             1275

Gly Gly  Gly Val Leu Leu Arg  Tyr Gly Ser Gln Leu  Ala Pro Glu
    1280             1285             1290

Thr Phe  Tyr Arg Glu Cys Asp  Met Gln Leu Phe Gly  Pro Trp Gly
    1295             1300             1305

Glu Ile  Val Ser Pro Ser Leu  Ser Pro Ala Thr Ser  Asn Ala Gly
    1310             1315             1320

Gly Cys  Arg Leu Phe Ile Asn  Val Ala Pro His Ala  Arg Ile Ala
    1325             1330             1335

Ile His  Ala Leu Ala Thr Asn  Met Gly Ala Gly Thr  Glu Gly Ala
    1340             1345             1350

Asn Ala  Ser Tyr Ile Leu Ile  Arg Asp Thr His Ser  Leu Arg Thr
    1355             1360             1365

Thr Ala  Phe His Gly Gln Gln  Val Leu Tyr Trp Glu  Ser Glu Ser
    1370             1375             1380

Ser Gln  Ala Glu Met Glu Phe  Ser Glu Gly Phe Leu  Lys Ala Gln
```

-continued

```
                1385                1390                1395

Ala Ser  Leu Arg Gly Gln Tyr  Trp Thr Leu Gln Ser  Trp Val Pro
    1400                1405                1410

Glu Met  Gln Asp Pro Gln Ser  Trp Lys Gly Lys Glu  Gly Thr
    1415                1420                1425

<210> SEQ ID NO 2
<211> LENGTH: 1371
<212> TYPE: PRT
<213> ORGANISM: Homo sapiens

<400> SEQUENCE: 2

Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
            20                  25                  30

Phe Gln Gln Ser Cys Leu Gln Ala Leu Glu Pro Gln Ala Val Ser Ser
        35                  40                  45

Tyr Leu Ser Pro Gly Ala Pro Leu Lys Gly Arg Pro Pro Ser Pro Gly
    50                  55                  60

Phe Gln Arg Gln Arg Gln Arg Gln Arg Ala Ala Gly Gly Ile Leu
65                  70                  75                  80

His Leu Glu Leu Leu Val Ala Val Gly Pro Asp Val Phe Gln Ala His
            85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
            165                 170                 175

Tyr Ile Thr Arg Phe Asp Leu Glu Leu Pro Asp Gly Asn Arg Gln Val
            180                 185                 190

Arg Gly Val Thr Gln Leu Gly Gly Ala Cys Ser Pro Thr Trp Ser Cys
        195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
            245                 250                 255

Arg Ala Gly Leu Ala Trp Ser Pro Cys Ser Arg Arg Gln Leu Leu Ser
            260                 265                 270

Leu Leu Ser Ala Gly Arg Ala Arg Cys Val Trp Asp Pro Pro Arg Pro
        275                 280                 285

Gln Pro Gly Ser Ala Gly His Pro Pro Asp Ala Gln Pro Gly Leu Tyr
    290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
            325                 330                 335
```

-continued

```
Cys His Thr Asp Pro Leu Asp Gln Ser Ser Cys Ser Arg Leu Leu Val
            340                 345                 350

Pro Leu Leu Asp Gly Thr Glu Cys Gly Val Glu Lys Trp Cys Ser Lys
            355                 360                 365

Gly Arg Cys Arg Ser Leu Val Glu Leu Thr Pro Ile Ala Ala Val His
        370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Arg Gln Cys Asn Asn Pro Arg Pro
                405                 410                 415

Ala Phe Gly Gly Arg Ala Cys Val Gly Ala Asp Leu Gln Ala Glu Met
            420                 425                 430

Cys Asn Thr Gln Ala Cys Glu Lys Thr Gln Leu Glu Phe Met Ser Gln
            435                 440                 445

Gln Cys Ala Arg Thr Asp Gly Gln Pro Leu Arg Ser Ser Pro Gly Gly
        450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
            485                 490                 495

Lys Arg Gly Asp Ser Phe Leu Asp Gly Thr Arg Cys Met Pro Ser Gly
            500                 505                 510

Pro Arg Glu Asp Gly Thr Leu Ser Leu Cys Val Ser Gly Ser Cys Arg
            515                 520                 525

Thr Phe Gly Cys Asp Gly Arg Met Asp Ser Gln Gln Val Trp Asp Arg
        530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
            595                 600                 605

Met Ser Ile Ser Pro Asn Thr Thr Tyr Pro Ser Leu Leu Glu Asp Gly
    610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655

Val Tyr Arg Arg Tyr Gly Glu Glu Tyr Gly Asn Leu Thr Arg Pro Asp
            660                 665                 670

Ile Thr Phe Thr Tyr Phe Gln Pro Lys Pro Arg Gln Ala Trp Val Trp
            675                 680                 685

Ala Ala Val Arg Gly Pro Cys Ser Val Ser Cys Gly Ala Gly Leu Arg
        690                 695                 700

Trp Val Asn Tyr Ser Cys Leu Asp Gln Ala Arg Lys Glu Leu Val Glu
705                 710                 715                 720

Thr Val Gln Cys Gln Gly Ser Gln Gln Pro Pro Ala Trp Pro Glu Ala
                725                 730                 735

Cys Val Leu Glu Pro Cys Pro Pro Tyr Trp Ala Val Gly Asp Phe Gly
            740                 745                 750

Pro Cys Ser Ala Ser Cys Gly Gly Gly Leu Arg Glu Arg Pro Val Arg
```

-continued

```
              755               760               765

Cys Val Glu Ala Gln Gly Ser Leu Leu Lys Thr Leu Pro Pro Ala Arg
         770               775               780

Cys Arg Ala Gly Ala Gln Gln Pro Ala Val Ala Leu Glu Thr Cys Asn
785               790               795               800

Pro Gln Pro Cys Pro Ala Arg Trp Glu Val Ser Glu Pro Ser Ser Cys
                   805               810               815

Thr Ser Ala Gly Gly Ala Gly Leu Ala Leu Glu Asn Glu Thr Cys Val
                   820               825               830

Pro Gly Ala Asp Gly Leu Glu Ala Pro Val Thr Glu Gly Pro Gly Ser
                   835               840               845

Val Asp Glu Lys Leu Pro Ala Pro Glu Pro Cys Val Gly Met Ser Cys
         850               855               860

Pro Pro Gly Trp Gly His Leu Asp Ala Thr Ser Ala Gly Glu Lys Ala
865               870               875               880

Pro Ser Pro Trp Gly Ser Ile Arg Thr Gly Ala Gln Ala Ala His Val
                   885               890               895

Trp Thr Pro Ala Ala Gly Ser Cys Ser Val Ser Cys Gly Arg Gly Leu
                   900               905               910

Met Glu Leu Arg Phe Leu Cys Met Asp Ser Ala Leu Arg Val Pro Val
                   915               920               925

Gln Glu Glu Leu Cys Gly Leu Ala Ser Lys Pro Gly Ser Arg Arg Glu
         930               935               940

Val Cys Gln Ala Val Pro Cys Pro Ala Arg Trp Gln Tyr Lys Leu Ala
945               950               955               960

Ala Cys Ser Val Ser Cys Gly Arg Gly Val Val Arg Arg Ile Leu Tyr
                   965               970               975

Cys Ala Arg Ala His Gly Glu Asp Asp Gly Glu Glu Ile Leu Leu Asp
                   980               985               990

Thr Gln Cys Gln Gly Leu Pro Arg Pro Glu Pro Gln Glu Ala Cys Ser
         995               1000              1005

Leu Glu Pro Cys Pro Pro Arg Trp Lys Val Met Ser Leu Gly Pro
         1010              1015              1020

Cys Ser Ala Ser Cys Gly Leu Gly Thr Ala Arg Arg Ser Val Ala
         1025              1030              1035

Cys Val Gln Leu Asp Gln Gly Gln Asp Val Glu Val Asp Glu Ala
         1040              1045              1050

Ala Cys Ala Ala Leu Val Arg Pro Glu Ala Ser Val Pro Cys Leu
         1055              1060              1065

Ile Ala Asp Cys Thr Tyr Arg Trp His Val Gly Thr Trp Met Glu
         1070              1075              1080

Cys Ser Val Ser Cys Gly Asp Gly Ile Gln Arg Arg Arg Asp Thr
         1085              1090              1095

Cys Leu Gly Pro Gln Ala Gln Ala Pro Val Pro Ala Asp Phe Cys
         1100              1105              1110

Gln His Leu Pro Lys Pro Val Thr Val Arg Gly Cys Trp Ala Gly
         1115              1120              1125

Pro Cys Val Gly Gln Gly Ala Cys Gly Arg Gln His Leu Glu Pro
         1130              1135              1140

Thr Gly Thr Ile Asp Met Arg Gly Pro Gly Gln Ala Asp Cys Ala
         1145              1150              1155

Val Ala Ile Gly Arg Pro Leu Gly Glu Val Val Thr Leu Arg Val
         1160              1165              1170
```

```
Leu Glu  Ser Ser Leu Asn Cys  Ser Ala Gly Asp Met  Leu Leu Leu
    1175             1180             1185

Trp Gly  Arg Leu Thr Trp Arg  Lys Met Cys Arg Lys  Leu Leu Asp
    1190             1195             1200

Met Thr  Phe Ser Ser Lys Thr  Asn Thr Leu Val Val  Arg Gln Arg
    1205             1210             1215

Cys Gly  Arg Pro Gly Gly Gly  Val Leu Leu Arg Tyr  Gly Ser Gln
    1220             1225             1230

Leu Ala  Pro Glu Thr Phe Tyr  Arg Glu Cys Asp Met  Gln Leu Phe
    1235             1240             1245

Gly Pro  Trp Gly Glu Ile Val  Ser Pro Ser Leu Ser  Pro Ala Thr
    1250             1255             1260

Ser Asn  Ala Gly Gly Cys Arg  Leu Phe Ile Asn Val  Ala Pro His
    1265             1270             1275

Ala Arg  Ile Ala Ile His Ala  Leu Ala Thr Asn Met  Gly Ala Gly
    1280             1285             1290

Thr Glu  Gly Ala Asn Ala Ser  Tyr Ile Leu Ile Arg  Asp Thr His
    1295             1300             1305

Ser Leu  Arg Thr Thr Ala Phe  His Gly Gln Gln Val  Leu Tyr Trp
    1310             1315             1320

Glu Ser  Glu Ser Ser Gln Ala  Glu Met Glu Phe Ser  Glu Gly Phe
    1325             1330             1335

Leu Lys  Ala Gln Ala Ser Leu  Arg Gly Gln Tyr Trp  Thr Leu Gln
    1340             1345             1350

Ser Trp  Val Pro Glu Met Gln  Asp Pro Gln Ser Trp  Lys Gly Lys
    1355             1360             1365

Glu Gly  Thr
    1370

<210> SEQ ID NO 3
<211> LENGTH: 1340
<212> TYPE: PRT
<213> ORGANISM: Homo sapiens

<400> SEQUENCE: 3

Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
                20                  25                  30

Phe Gln Gln Ser Cys Leu Gln Ala Leu Glu Pro Gln Ala Val Ser Ser
            35                  40                  45

Tyr Leu Ser Pro Gly Ala Pro Leu Lys Gly Arg Pro Pro Ser Pro Gly
        50                  55                  60

Phe Gln Arg Gln Arg Gln Arg Gln Arg Ala Ala Gly Gly Ile Leu
65              70                  75                  80

His Leu Glu Leu Leu Val Ala Val Gly Pro Asp Val Phe Gln Ala His
                85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
```

-continued

```
145              150              155              160

Ile Asn Pro Glu Asp Asp Thr Asp Pro Gly His Ala Asp Leu Val Leu
                165              170              175

Tyr Ile Thr Arg Phe Asp Leu Glu Leu Pro Asp Gly Asn Arg Gln Val
                180              185              190

Arg Gly Val Thr Gln Leu Gly Gly Ala Cys Ser Pro Thr Trp Ser Cys
                195              200              205

Leu Ile Thr Glu Asp Thr Gly Phe Asp Leu Gly Val Thr Ile Ala His
    210              215              220

Glu Ile Gly His Ser Phe Gly Leu Glu His Asp Gly Ala Pro Gly Ser
225              230              235              240

Gly Cys Gly Pro Ser Gly His Val Met Ala Ser Asp Gly Ala Ala Pro
                245              250              255

Arg Ala Gly Leu Ala Trp Ser Pro Cys Ser Arg Arg Gln Leu Leu Ser
                260              265              270

Leu Leu Ser Ala Asn Glu Gln Cys Arg Val Ala Phe Gly Pro Lys Ala
                275              280              285

Val Ala Cys Thr Phe Ala Arg Glu His Leu Asp Met Cys Gln Ala Leu
    290              295              300

Ser Cys His Thr Asp Pro Leu Asp Gln Ser Ser Cys Ser Arg Leu Leu
305              310              315              320

Val Pro Leu Leu Asp Gly Thr Glu Cys Gly Val Glu Lys Trp Cys Ser
                325              330              335

Lys Gly Arg Cys Arg Ser Leu Val Glu Leu Thr Pro Ile Ala Ala Val
                340              345              350

His Gly Arg Trp Ser Ser Trp Gly Pro Arg Ser Pro Cys Ser Arg Ser
                355              360              365

Cys Gly Gly Gly Val Val Thr Arg Arg Arg Gln Cys Asn Asn Pro Arg
    370              375              380

Pro Ala Phe Gly Gly Arg Ala Cys Val Gly Ala Asp Leu Gln Ala Glu
385              390              395              400

Met Cys Asn Thr Gln Ala Cys Glu Lys Thr Gln Leu Glu Phe Met Ser
                405              410              415

Gln Gln Cys Ala Arg Thr Asp Gly Gln Pro Leu Arg Ser Ser Pro Gly
                420              425              430

Gly Ala Ser Phe Tyr His Trp Gly Ala Ala Val Pro His Ser Gln Gly
                435              440              445

Asp Ala Leu Cys Arg His Met Cys Arg Ala Ile Gly Glu Ser Phe Ile
    450              455              460

Met Lys Arg Gly Asp Ser Phe Leu Asp Gly Thr Arg Cys Met Pro Ser
465              470              475              480

Gly Pro Arg Glu Asp Gly Thr Leu Ser Leu Cys Val Ser Gly Ser Cys
                485              490              495

Arg Thr Phe Gly Cys Asp Gly Arg Met Asp Ser Gln Gln Val Trp Asp
                500              505              510

Arg Cys Gln Val Cys Gly Gly Asp Asn Ser Thr Cys Ser Pro Arg Lys
                515              520              525

Gly Ser Phe Thr Ala Gly Arg Ala Arg Glu Tyr Val Thr Phe Leu Thr
    530              535              540

Val Thr Pro Asn Leu Thr Ser Val Tyr Ile Ala Asn His Arg Pro Leu
545              550              555              560

Phe Thr His Leu Ala Val Arg Ile Gly Gly Arg Tyr Val Val Ala Gly
                565              570              575
```

```
Lys Met Ser Ile Ser Pro Asn Thr Thr Tyr Pro Ser Leu Leu Glu Asp
        580                 585                 590

Gly Arg Val Glu Tyr Arg Val Ala Leu Thr Glu Asp Arg Leu Pro Arg
        595                 600                 605

Leu Glu Glu Ile Arg Ile Trp Gly Pro Leu Gln Glu Asp Ala Asp Ile
        610                 615                 620

Gln Val Tyr Arg Arg Tyr Gly Glu Glu Tyr Gly Asn Leu Thr Arg Pro
625                 630                 635                 640

Asp Ile Thr Phe Thr Tyr Phe Gln Pro Lys Pro Arg Gln Ala Trp Val
                645                 650                 655

Trp Ala Ala Val Arg Gly Pro Cys Ser Val Ser Cys Gly Ala Gly Leu
                660                 665                 670

Arg Trp Val Asn Tyr Ser Cys Leu Asp Gln Ala Arg Lys Glu Leu Val
                675                 680                 685

Glu Thr Val Gln Cys Gln Gly Ser Gln Gln Pro Pro Ala Trp Pro Glu
        690                 695                 700

Ala Cys Val Leu Glu Pro Cys Pro Pro Tyr Trp Ala Val Gly Asp Phe
705                 710                 715                 720

Gly Pro Cys Ser Ala Ser Cys Gly Gly Gly Leu Arg Glu Arg Pro Val
                725                 730                 735

Arg Cys Val Glu Ala Gln Gly Ser Leu Leu Lys Thr Leu Pro Pro Ala
                740                 745                 750

Arg Cys Arg Ala Gly Ala Gln Gln Pro Ala Val Ala Leu Glu Thr Cys
        755                 760                 765

Asn Pro Gln Pro Cys Pro Ala Arg Trp Glu Val Ser Glu Pro Ser Ser
        770                 775                 780

Cys Thr Ser Ala Gly Gly Ala Gly Leu Ala Leu Glu Asn Glu Thr Cys
785                 790                 795                 800

Val Pro Gly Ala Asp Gly Leu Glu Ala Pro Val Thr Glu Gly Pro Gly
                805                 810                 815

Ser Val Asp Glu Lys Leu Pro Ala Pro Glu Pro Cys Val Gly Met Ser
        820                 825                 830

Cys Pro Pro Gly Trp Gly His Leu Asp Ala Thr Ser Ala Gly Glu Lys
        835                 840                 845

Ala Pro Ser Pro Trp Gly Ser Ile Arg Thr Gly Ala Gln Ala Ala His
        850                 855                 860

Val Trp Thr Pro Ala Ala Gly Ser Cys Ser Val Ser Cys Gly Arg Gly
865                 870                 875                 880

Leu Met Glu Leu Arg Phe Leu Cys Met Asp Ser Ala Leu Arg Val Pro
                885                 890                 895

Val Gln Glu Glu Leu Cys Gly Leu Ala Ser Lys Pro Gly Ser Arg Arg
                900                 905                 910

Glu Val Cys Gln Ala Val Pro Cys Pro Ala Arg Trp Gln Tyr Lys Leu
        915                 920                 925

Ala Ala Cys Ser Val Ser Cys Gly Arg Gly Val Val Arg Arg Ile Leu
        930                 935                 940

Tyr Cys Ala Arg Ala His Gly Glu Asp Asp Gly Glu Glu Ile Leu Leu
945                 950                 955                 960

Asp Thr Gln Cys Gln Gly Leu Pro Arg Pro Glu Pro Gln Glu Ala Cys
                965                 970                 975

Ser Leu Glu Pro Cys Pro Pro Arg Trp Lys Val Met Ser Leu Gly Pro
        980                 985                 990
```

-continued

```
Cys Ser Ala Ser Cys Gly Leu Gly  Thr Ala Arg Arg Ser  Val Ala Cys
        995              1000              1005

Val Gln  Leu Asp Gln Gly Gln  Asp Val Glu Val Asp  Glu Ala Ala
    1010              1015              1020

Cys Ala  Ala Leu Val Arg Pro  Glu Ala Ser Val Pro  Cys Leu Ile
    1025              1030              1035

Ala Asp  Cys Thr Tyr Arg Trp  His Val Gly Thr Trp  Met Glu Cys
    1040              1045              1050

Ser Val  Ser Cys Gly Asp Gly  Ile Gln Arg Arg Arg  Asp Thr Cys
    1055              1060              1065

Leu Gly  Pro Gln Ala Gln Ala  Pro Val Pro Ala Asp  Phe Cys Gln
    1070              1075              1080

His Leu  Pro Lys Pro Val Thr  Val Arg Gly Cys Trp  Ala Gly Pro
    1085              1090              1095

Cys Val  Gly Gln Gly Ala Cys  Gly Arg Gln His Leu  Glu Pro Thr
    1100              1105              1110

Gly Thr  Ile Asp Met Arg Gly  Pro Gly Gln Ala Asp  Cys Ala Val
    1115              1120              1125

Ala Ile  Gly Arg Pro Leu Gly  Glu Val Val Thr Leu  Arg Val Leu
    1130              1135              1140

Glu Ser  Ser Leu Asn Cys Ser  Ala Gly Asp Met Leu  Leu Leu Trp
    1145              1150              1155

Gly Arg  Leu Thr Trp Arg Lys  Met Cys Arg Lys Leu  Leu Asp Met
    1160              1165              1170

Thr Phe  Ser Ser Lys Thr Asn  Thr Leu Val Val Arg  Gln Arg Cys
    1175              1180              1185

Gly Arg  Pro Gly Gly Gly Val  Leu Leu Arg Tyr Gly  Ser Gln Leu
    1190              1195              1200

Ala Pro  Glu Thr Phe Tyr Arg  Glu Cys Asp Met Gln  Leu Phe Gly
    1205              1210              1215

Pro Trp  Gly Glu Ile Val Ser  Pro Ser Leu Ser Pro  Ala Thr Ser
    1220              1225              1230

Asn Ala  Gly Gly Cys Arg Leu  Phe Ile Asn Val Ala  Pro His Ala
    1235              1240              1245

Arg Ile  Ala Ile His Ala Leu  Ala Thr Asn Met Gly  Ala Gly Thr
    1250              1255              1260

Glu Gly  Ala Asn Ala Ser Tyr  Ile Leu Ile Arg Asp  Thr His Ser
    1265              1270              1275

Leu Arg  Thr Thr Ala Phe His  Gly Gln Gln Val Leu  Tyr Trp Glu
    1280              1285              1290

Ser Glu  Ser Ser Gln Ala Glu  Met Glu Phe Ser Glu  Gly Phe Leu
    1295              1300              1305

Lys Ala  Gln Ala Ser Leu Arg  Gly Gln Tyr Trp Thr  Leu Gln Ser
    1310              1315              1320

Trp Val  Pro Glu Met Gln Asp  Pro Gln Ser Trp Lys  Gly Lys Glu
    1325              1330              1335

Gly Thr
    1340
```

ADAMTS13 TREATMENT TO ENHANCE GRAFT SURVIVAL

CROSS-REFERENCE TO RELATED APPLICATIONS

This application is a 35 U.S.C. § 371 National Phase Entry Application of International Patent Application No. PCT/US2020/053901 filed on Oct. 2, 2020, which designated the U.S., and which claims benefit under 35 U.S.C. § 119(e) of U.S. Provisional Application No. 62/911,019 filed Oct. 4, 2019, the contents of which are incorporated herein by reference in their entireties.

STATEMENT AS TO FEDERALLY SPONSORED RESEARCH

This invention was made with government support under HL135765 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 1, 2020, is named 701039-098350WO-PT_SL.txt and is 36,163 bytes in size.

FIELD OF THE INVENTION

The disclosure relates to a method treating or preventing graft rejection and/or increasing graft survival in a subject that received a graft, the method comprising administering to the subject in need thereof a therapeutically effective amount of a composition comprising A Disintegrin And Metalloproteinase with Thrombospondin type 1 motif, member-13 (ADAMTS13). In certain embodiments, the disclosure relates to a method for increasing ADAMTS13-mediated von Willebrand factor (VWF) cleavage in a subject that received a graft by administering ADAMTS13 to treating or preventing graft rejection and/or increasing graft survival. The disclosure further relates to a method for determining the likelihood that a graft will be rejected by a subject.

BACKGROUND OF THE INVENTION

Allogeneic skin transplant is a preferred first-line therapy for burn patients, in particular for those whose wounds do not have sufficient blood vessels to take autologous split-thickness skin grafts. Allografts not only serve as temporary dressings for burn wounds, they also prepare the wound bed for replacement with autografts later, such as by providing the wound bed with critical growth factors and cytokines for vascularization. In addition, unlike the civilian population which can be transported to a burn center within 24 hours after injury, combat-related burn wounds are not easily treated in a timely way. The average time for injured soldiers to receive optimal wound treatment is around 5 days. Immediate proper wound care, including skin allograft transplantation from deceased donors on location, is of paramount value before further medical or surgical intervention is available. Survival of an individual after severe burn injury is associated with good allograft tolerance.

In addition to alloimmunity conferred by activated lymphocytes, microthrombosis may also be a key factor contributing to allograft rejection. A Disintegrin and Metalloproteinase with a Thrombospondin Type 1 Motif, Member 13 (ADAMTS13) is a plasma metalloprotease that cleaves ultra-large von Willebrand factor (UL-VWF), which is highly pro-inflammatory and pro-thrombotic. Patients receiving liver transplant had significantly reduced plasma ADAMTS13 activity and elevated levels of UL-VWF multimers in the circulation. These changes were associated with post-transplant liver dysfunction, such as ischemia/reperfusion injury and acute rejection. Because organ deterioration was restricted to the transplanted liver, it could possibly be due to severe local microthrombosis. Indeed, VWF expression was elevated in grafted livers that were acutely rejected due to allogeneic immune response.

VWF also promotes neutrophil recruitment and binds to neutrophil extracellular traps (NETs). Formation of NETs (NETosis) is mediated by peptidylarginine deiminase 4 (PAD4). By citrullinating arginine residues on histones, PAD4 massively decondenses the chromatin prior to NET release. NETs are lined with cytotoxic proteins, causing tissue damages, delaying wound healing, and even aggravating sepsis. Intriguingly, NETs were present in the lungs of mice subjected to orthotopic lung transplant, and were at higher levels in the bronchoalveolar lavage fluid of patients suffering severe primary graft dysfunction after lung transplant compared to patients free of the dysfunction. Disruption of NETs by DNase 1 rescued the function of the lung allografts in mice, indicating a pathogenic role of NETs in allograft failure.

Thus, there is a need in the art for improved treatments to prevent graft (e.g., allograft) rejections, including the treatment that can reduce symptoms, prevent complications (e.g., inflammation, microthrombosis etc.), and improve graft longevity, as well as useful clinical biomarkers for graft rejection.

SUMMARY OF THE INVENTION

As specified in the Background section above, there is a great need in the art for diagnosing, preventing and/or treating graft rejection. The present application addresses these and other needs.

In one aspect, the present disclosure provides a method for treating or preventing graft rejection in a subject that received a graft, the method comprising administering to the subject in need thereof a therapeutically effective amount of a composition comprising A Disintegrin And Metalloproteinase with Thrombospondin type 1 motif, member-13 (ADAMTS13). In certain embodiments, the method further comprises reduced or eliminated gene(s) or gene product(s) of PAD4, H3Cit, H4Cit, MPO, NE, or NLRP3. In certain embodiments, the method further comprises inhibiting NET formation and/or neutrophil infiltration.

In another aspect, the present disclosure provides a method for increasing graft survival in a subject that received a graft, the method comprising administering to the subject in need thereof a therapeutically effective amount of a composition comprising ADAMTS13. In certain embodiments, the method further comprises reduced or eliminated gene(s) or gene product(s) of PAD4, H3Cit, H4Cit, MPO, NE, or NLRP3. In certain embodiments, the method further comprises inhibiting NET formation and/or neutrophil infiltration.

In yet another aspect, the present disclosure provides a method for determining the likelihood that a graft will be rejected by a subject, the method comprising: (a) determining the level of NET and/or PAD4 in the graft, or a CSF or a blood sample obtained from the subject before the graft is transplanted, (b) determining the level of NET and/or PAD4 in the graft, or the CSF or a blood sample obtained from the subject after the graft is transplanted, (c) comparing the levels determined in steps (a) and (b), and (d) determining that the subject is at risk for rejecting the graft if the level of NET and/or PAD4 in the graft, or the CSF or the blood of the subject has increased after the graft is transplanted as compared to a control. In certain embodiments, the method further comprises administering ADAMTS13. In certain embodiments, the method further comprises modifying one or more additional genes or gene products such that the expression and/or function of said additional gene(s) or gene product(s) is reduced or eliminated. In certain embodiments, said additional gene(s) or gene product(s) are gene(s) or gene product(s) of PAD4, H3Cit, H4Cit, MPO, NE, or NLRP3. In certain embodiments, the method further comprises inhibiting NET formation and/or neutrophil infiltration.

In yet another aspect, the present disclosure provides a method for determining the likelihood that a graft will be rejected by a subject, the method comprising: (a) determining the level of NET and/or PAD4 in the graft, or a CSF or a blood sample obtained from the subject after the graft is transplanted, (b) determining the level of NET and/or PAD4 in the same tissue as the graft in step (a), or the CSF or a blood sample obtained from a control, (c) comparing the levels determined in steps (a) and (b), and (d) determining that the subject is at risk for rejecting the graft if the level of NET and/or PAD4 in the graft, or the CSF or the blood of the subject is higher in the graft as compared to a control. In certain embodiments, the method further comprises administering ADAMTS13. In certain embodiments, the method further comprises reduced or eliminated gene(s) or gene product(s) of PAD4, H3Cit, H4Cit, MPO, NE, or NLRP3. In certain embodiments, the method further comprises inhibiting NET formation and/or neutrophil infiltration.

In certain embodiments, the graft is a skin, cells, bone, nerves, tendons, neurons, blood vessels, fat, or cornea graft. In certain embodiments, the graft is a skin graft.

In certain embodiments, the graft is an allograft, autograft, isograft, or xenograft. In certain embodiments, the graft is an allograft.

DESCRIPTION OF THE FIGURES

FIG. 1A outlines the experimental design. FIG. 1B shows the effects of exogenous ADAMTS13 on skin allograft survival on day 7 and day 10 following the skin transplant; the right panel of FIG. 1B show an associated survival curve. FIG. 1C is a Western blot and evaluation of neutrophil levels (indicated by MPO) in the mouse allograft with and without ADAMTS13 treatment. FIG. 1D is a Western blot and evaluation of NET (indicated by H4Cit) levels in the mouse allograft with and without ADAMTS13 treatment. FIG. 1E is immunofluorescence staining of neutrophil and NET (indicated by H4Cit) localization in the mouse allografts with and without ADAMTS13 treatment.

FIG. 2A is a Western blot and evaluation of neutrophil (indicated by neutrophil elastase, NE) levels in the allografts of burn patients with and without ADAMTS13 treatment. FIG. 2B is a Western blot and evaluation of NET (indicated by H4Cit) levels in the allografts of burn patients with and without ADAMTS13 treatment.

FIG. 2C is immunofluorescence staining of NETs (H3Cit+ and MPO+ extracellular DNA) localization in the human allografts. FIG. 2D shows mean allograft survival in wild-type and Padi4−/− recipients. FIG. 2E shows mean allograft survival in wild-type and Padi4−/− recipients with and without ADAMTS13 treatment. FIG. 2F shows mean allograft survival in wild-type recipients with and without DNase 1 treatment.

DETAILED DESCRIPTION OF THE INVENTION

Figure 1A:
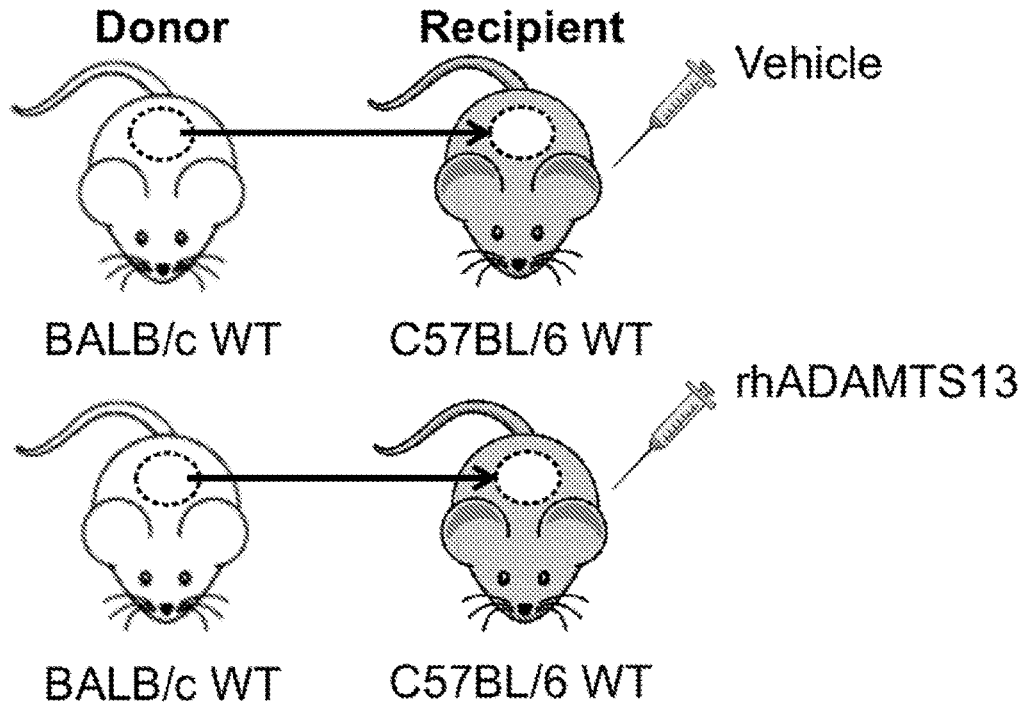
FIGS. 1A-1E shows the survival rate of mouse allografts.

The disclosure provides, in various aspects, ADAMTS13 and related methods for preventing, ameliorating, and/or treating graft rejection and/or increasing graft survival. Before any embodiments of the disclosure are explained in detail, it is to be understood that the invention is not limited in its application to the details of construction and the arrangement of components set forth in the following description or illustrated in the figures and examples. The section headings used herein are for organizational purposes only and are not to be construed as limiting the subject matter described. All references cited in this application are expressly incorporated by reference herein for all purposes.

The disclosure embraces other embodiments and is practiced or carried out in various ways. Also, it is to be understood that the phraseology and terminology used herein is for the purpose of description and should not be regarded as limiting. The terms "including," "comprising," or "having" and variations thereof are meant to encompass the items listed thereafter and equivalents thereof as well as additional items.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention. The following abbreviations are used throughout.

ADAMTS13 A Disintegrin And Metalloproteinase with Thrombospondin type 1 motif, member-13

H3Cit Citrullinated histone H3

H4Cit Citrullinated histone H4

MPO Myeloperoxidase

NETs Neutrophil extracellular traps

NE Neutrophil elastase

PAD4 Peptidylarginine deiminase 4

Padi4−/− Mice deficient in peptidylarginine deiminase 4 rhADAMTS13 Recombinant human ADAMTS13

UL-VWF Ultra-large von Willebrand factor

VWF von Willebrand factor

WT Wild-type

It is noted here that, as used in this specification and the appended claims, the singular forms "a," "an," and "the" include plural reference unless the context clearly dictates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example." With respect to aspects of the disclosure described as a genus, all individual species are considered separate aspects of the disclosure. If aspects of the disclosure are described as "comprising" a feature, embodiments also are contemplated "consisting of" or "consisting essentially of" the feature.

As used herein, the following terms have the meanings ascribed to them unless specified otherwise.

"A disintegrin and metalloproteinase with a thrombospondin type 1 motif, member 13 (ADAMTS13)" is also known as von Willebrand factor-cleaving protease (VWFCP). The term "ADAMTS13" or "ADAMTS13 protein," as used herein, includes ADAMTS13 analogs, variants, derivatives (including chemically-modified derivatives) and fragments thereof. In some aspects, the analogs, variants, derivatives, and fragments thereof have increased biological activity compared to ADAMTS13. In various aspects, ADAMTS13 is recombinant ADAMTS13 (rADAMTS13) or is blood-derived ADAMTS13, including plasma- and serum-derived ADAMTS13.

As used herein, an "analog" refers to a polypeptide, e.g., ADAMTS13, substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide (including fragments as described above) and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence. Substitutions are conservative or non-conservative based on the physico-chemical or functional relatedness of the amino acid that is being replaced and the amino acid replacing it.

"Conservatively modified analogs" applies to both amino acid and nucleic acid sequences. With respect to particular nucleic acid sequences, conservatively modified nucleic acids refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified analogs. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, insertions, deletions, additions, or truncations to a nucleic acid, peptide, polypeptide, or protein sequence which alters, adds or deletes a single amino acid or a small percentage of amino acids in the encoded sequence is a "conservatively modified analog" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

As used herein, a "variant" refers to a polypeptide, protein or analog thereof that comprises at least one amino acid substitution, deletion, insertion, or modification, provided that the variant retains the biological activity of the native polypeptide. The term "variant," in some aspects, is interchangeably used with the term "mutant."

As used herein, an "allelic variant" refers to any of two or more polymorphic forms of a gene occupying the same genetic locus. Allelic variations arise naturally through mutation and, in some aspects, result in phenotypic polymorphism within populations. In certain aspects, gene mutations are silent (no change in the encoded polypeptide) or, in other aspects, encode polypeptides having altered amino acid sequences. "Allelic variants" also refer to cDNAs derived from mRNA transcripts of genetic allelic variants, as well as the proteins encoded by them.

The term "derivative" refers to polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some aspects, derivatives are modified to comprise additional chemical moieties not normally a part of the molecule. In certain aspects, these derivatives are called chemically-modified derivatives. Such moieties, in various aspects, modulate the molecule's solubility, absorption, and/or biological half-life. The moieties, in various other aspects, alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. For example, in some aspects, an ADAMTS13 derivative is an ADAMTS13 molecule having a chemical modification which confers a longer half-life in vivo to the protein. In one embodiment, the polypeptides are modified by addition of a water-soluble polymer known in the art. In a related embodiment, polypeptides are modified by glycosylation, PEGylation, and/or polysialylation.

As used herein, a "fragment" of a polypeptide refers to any portion of the polypeptide smaller than the full-length polypeptide or protein expression product. Fragments are typically deletion analogs of the full-length polypeptide, wherein one or more amino acid residues have been removed from the amino terminus and/or the carboxy terminus of the full-length polypeptide. Accordingly, "fragments" are a subset of deletion analogs described below. In some embodiments, the polypeptide described herein (or a nucleic acid encoding such a polypeptide) can be a functional fragment of one of the amino acid sequences described herein. As used herein, a "functional fragment" is a fragment or segment of a polypeptide which retains at least 50% of the wild-type reference polypeptide's activity according to the assays described below herein. A functional fragment can comprise conservative substitutions of the sequences disclosed herein.

The term "recombinant" or "recombinant expression system" when used with reference, e.g., to a cell, indicates that the cell has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "recombinant," when used herein to refer to a polypeptide or protein, means that a polypeptide or protein is derived from recombinant (e.g., microbial or mammalian) expression systems. "Microbial" refers to recombinant polypeptides or proteins made in bacterial or fungal (e.g., yeast) expression systems. The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest may be found by comparing the sequence of the particular polypeptide with that of homologous peptides and minimizing the number of amino acid sequence changes made in regions of high homology.

The term "agent" or "compound" describes any molecule, e.g., protein or pharmaceutical, with the capability of affecting a biological parameter in the disclosure.

A "control," as used herein, can refer to an active, positive, negative or vehicle control. As will be understood by those of skill in the art, controls are used to establish the relevance of experimental results, and provide a comparison for the condition being tested. In certain aspects, a control is a subject that does not receive an active prophylactic or therapeutic composition. In certain aspects, a control is a subject not experiencing graft rejection, for example, but not limited to a healthy control or a subject without any symptoms.

The terms "increase" or "improve" when referring to survival and/or function, means that the survival or function of the graft, organ and/or subject has been increased and/or improved as compared to control, the subject prior to treatment, and/or the subject prior to transplant. In that case, a composition or treatment can be said to increase and/or improved the survival and/or function of the graft, organ and/or subject by about 10%, about 15%, about 20%, about 25%, about 30%, about 35%, about 40%, about 50%, about 60%, about 70%, about 80%, about 90%, or about 100% as compared to the control, the subject prior to treatment, and/or the subject prior to transplant. In certain aspects, a composition or treatment can be said to increase and/or improved the survival and/or function of the graft, organ and/or subject if the survival and/or function is increased and/or improved between about 10% to about 100%, about 20% to about 90%, about 30% to about 80%, about 40% to about 70% or about 50% to about 60%, as compared to the control, the subject prior to treatment, and/or the subject prior to transplant. In certain aspects, a composition or treatment can be said to increase and/or improved the survival and/or function of the graft, organ and/or subject if the survival and/or function is increased and/or improved between about 10% to about 30%, about 20% to about 40%, about 30% to about 50%, about 40% to about 60%, about 50% to about 70%, about 60% to about 80%, about 70% to about 90% or about 80% to about 100%, as compared to the control, the subject prior to treatment, and/or the subject prior to transplant.

The term "reduce" when referring to, for example, a symptom, cause and/or consequence of graft rejection means that the symptom, cause and/or consequence has delayed onset, reduced severity, reduced frequency, or causes less damage to the subject. Symptoms, causes, and/or consequences include, but are not limited to, pain, inflammation, graft deterioration, graft desiccation, graft shrinkage, scab formation, graft hardening, loss of hair, draft dysfunction, organ deterioration, organ damage, organ dysfunction, cell damage, inflammation, swelling, erythema, seroma, infection, NET burden, neutrophil recruitment, lymphocyte recruitment, platelet aggregation, microthrombosis, generation of inappropriate angiogenesis. Generally, severity of a symptom, cause and/or consequence is compared to a control, the subject prior to treatment, and/or the subject prior to transplant. In that case, a composition can be said to reduce the severity of a symptom, cause and/or consequence, if the symptom, cause and/or consequence is reduced by about 10%, about 15%, about 20%, about 25%, about 30%, about 35%, about 40%, about 50%, about 60%, about 70%, about 80%, about 90%, or about 100% (i.e., essentially eliminated), as compared to the control level of the symptom, the subject prior to treatment, and/or the subject prior to transplant. In certain aspects, a composition can be said to reduce the severity of a symptom, cause and/or consequence if the symptom, cause and/or consequence is reduced between about 10% to about 100%, about 20% to about 90%, about 30% to about 80%, about 40% to about 70% or about 50% to about 60%, as compared to the control level of the symptom, the subject prior to treatment, and/or the subject prior to transplant. In certain aspects, a composition can be said to reduce the severity of a symptom, cause and/or consequence if the symptom, cause and/or consequence is reduced between about 10% to about 30%, about 20% to about 40%, about 30% to about 50%, about 40% to about 60%, about 50% to about 70%, about 60% to about 80%, about 70% to about 90% or about 80% to about 100%, as compared to the control level of the symptom, the subject prior to treatment, and/or the subject prior to transplant.

The term "reduce" as it pertains to expression, level, and/or activation when referring to a biomarker of graft rejection (for example, but not limited to levels of NET burden, neutrophil infiltration, and/or PAD4), means that the expression, level, and/or activation of a biomarker has been reduced as compared to control, the subject prior to treatment, and/or the subject prior to transplant. In that case, reduced expression, level, and/or activation of a biomarker is reduced by about 10%, about 15%, about 20%, about 25%, about 30%, about 35%, about 40%, about 50%, about 60%, about 70%, about 80%, about 90%, or about 100% (i.e., essentially eliminated), as compared to the control, the subject prior to treatment, and/or the subject prior to transplant. In certain aspects, reduced expression, level, and/or activation of the biomarker is reduced between about 10% to about 100%, about 20% to about 90%, about 30% to about 80%, about 40% to about 70% or about 50% to about 60%, as compared to the control, the subject prior to treatment, and/or the subject prior to transplant. In certain aspects, reduce the expression, level, and/or activation is reduced between about 10% to about 30%, about 20% to about 40%, about 30% to about 50%, about 40% to about 60%, about 50% to about 70%, about 60% to about 80%, about 70% to about 90% or about 80% to about 100%, as compared to the control, the subject prior to treatment, and/or the subject prior to transplant.

The terms "increase" as it pertains to expression, level, and activation when referring to a biomarker of graft rejection (for example, but not limited to levels of NET burden, neutrophil infiltration, and/or PAD4), means that the expression, level, and/or activation of a biomarker has been increased as compared to control, the subject prior to treatment, and/or the subject prior to transplant. In that case, the expression, level, and/or activation of a biomarker is increased by about 10%, about 15%, about 20%, about 25%, about 30%, about 35%, about 40%, about 50%, about 60%, about 70%, about 80%, about 90%, or about 100%, as compared to the control, the subject prior to treatment, and/or the subject prior to transplant. In certain aspects, the expression, level, and/or activation of the biomarker is increased between about 10% to about 100%, about 20% to about 90%, about 30% to about 80%, about 40% to about 70% or about 50% to about 60%, as compared to the control, the subject prior to treatment, and/or the subject prior to transplant. In certain aspects, the expression, level, and/or activation is increased between about 10% to about 30%, about 20% to about 40%, about 30% to about 50%, about 40% to about 60%, about 50% to about 70%, about 60% to about 80%, about 70% to about 90% or about 80% to about 100%, as compared to the control, the subject prior to treatment, and/or the subject prior to transplant.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. graft rejection. The term "treating" includes reducing or alleviating at least one adverse effect or symptom of a condition, disease or disorder associated with graft rejection. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in or within nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

The terms "effective amount" and "therapeutically effective amount" each refer to the amount of polypeptide, e.g., ADAMTS13 polypeptide, or composition used to support an observable level of one or more biological activities of the ADAMTS13 polypeptide, as set forth herein. For example, an effective amount, in some aspects of the disclosure, would be the amount necessary to treat or prevent symptoms of graft rejection.

A "subject" is given its conventional meaning of a non-plant, non-protist living being. In most aspects, the subject is an animal. In particular aspects, the animal is a mammal. In more particular aspects, the mammal is a human. In other aspects, the mammal is a pet or companion animal, a domesticated farm animal, or a zoo animal. In certain aspects, the mammal is a mouse, rat, rabbit, guinea pig, pig, or non-human primate. In particular aspects, the animal is a mouse. In other aspects the mammal is a cat, dog, horse, or cow. In various other aspects, the mammal is a deer, mouse, chipmunk, squirrel, opossum, or raccoon. A "subject in need" of treatment for a particular condition can be a subject having that condition, diagnosed as having that condition, or at risk of developing that condition.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as about 1% to 50%, it is intended that values such as 2% to 40%, 10% to 30%, or 1% to 3%, etc., are expressly enumerated in this specification. The values listed above are only examples of what is specifically intended.

Ranges, in various aspects, are expressed herein as from "about" or "approximately" one particular value and/or to "about" or "approximately" another particular value. When values are expressed as approximations, by use of the antecedent "about," it will be understood that some amount of variation is included in the range. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The term "statistically significant" or "significantly" refers to statistical significance and generally means a two standard deviation (2SD) or greater difference.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in cell biology, immunology, and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

ADAMTS13

In some aspects, the disclosure includes ADAMTS13 (also known as "A13") and compositions comprising ADAMTS13 in the treatment and/or prevention of graft rejection. The ADAMTS13 protease is about a 180 kDa to 200 kDa glycosylated protein produced predominantly by the liver. ADAMTS13 is a plasma metalloprotease which cleaves VWF multimers and down regulates their activity in platelet aggregation. To date, ADAMTS13 has been associated with clotting disorders, such as inherited thrombotic thrombocytopenic purpura (TTP), acquired TTP, cerebral infarction, myocardial infarction, ischemic/reperfusion injury, deep vein thrombosis, and disseminated intravascular coagulation (DIC), such as sepsis-related DIC.

All forms of ADAMTS13 known in the art are contemplated for use in the methods and uses of the disclosure. Mature ADAMTS13 has a calculated molecular mass of about 145 kDa whereas purified plasma-derived ADAMTS13 has an apparent molecular mass of about 180 kDa to 200 kDa, probably due to post-translational modifications consisting with present consensus sequences for 10 potential N-glycosylation sites, and several O-glycosylation sites and one C-mannosylation site in the TSP1 repeats.

As used herein, "ADAMTS13" refers to a metalloprotease of the ADAMTS (a disintegrin and metalloproteinase with thrombospondin type 1 motifs) family that cleaves VWF in the A2 domain between residues $Tyr^{1605}$ and $Met^{1606}$. In the context of the disclosure, "ADAMTS13", "A13", or an "ADAMTS13 protein" embraces any ADAMTS13 protein, for example, ADAMTS13 from a mammal such as a primate, human (NP620594), monkey, rabbit, pig, bovine (XP610784), rodent, mouse (NP001001322), rat (XP342396), hamster, gerbil, canine, feline, frog (NP001083331), chicken (XP415435), and biologically active derivatives thereof. As used herein, "ADAMTS13", "A13", or "ADAMTS13 protein" refers to recombinant, natural, or plasma-derived ADAMTS13 protein. Mutant and variant ADAMTS13 proteins having activity are also embraced, as are functional fragments and fusion proteins of the ADAMTS13 proteins. In some aspects, an ADAMTS13 protein further comprises a tag that facilitates purification, detection, or both. The ADAMTS13 protein of the disclosure, in some aspects, is further modified with an additional therapeutic moiety or a moiety suitable imaging in vitro or in vivo.

ADAMTS13 protein includes any protein or polypeptide with ADAMTS13 activity, particularly the ability to cleave the peptide bond between residues Tyr-842 and Met-843 of VWF. Human ADAMTS13 proteins include, without limitation, polypeptides comprising the amino acid sequence of GenBank accession number NP 620594 (NM139025.3; e.g., SEQ ID NO: 1) or a processed polypeptide thereof, for example a polypeptide in which the signal peptide (amino acids 1 to 29, e.g., of one of SEQ ID NOs: 1-3) and/or propeptide (amino acids 30-74 of one of SEQ ID NOs: 1-3) have been removed (e.g., from one of SEQ ID NOs: 1-3). In certain aspects, an ADAMTS13 protein refers to a polypeptide comprising an amino acid sequence that is highly similar to amino acids 75 to 1427 of NP_620594 (ADAMTS13 isoform 1, mature polypeptide; e.g., residues 75-1427 of SEQ ID NO: 1). In certain aspects, an ADAMTS13 protein refers to a polypeptide comprising an amino acid sequence that is highly similar to that of NP 620596 (ADAMTS13 isoform 2, preproprotein; e.g., SEQ ID NO: 2) or amino acids 75 to 1371 of NP_620594 (ADAMTS13 isoform 2, mature polypeptide). In certain aspects, an ADAMTS13 protein refers to a polypeptide comprising an amino acid sequence that is highly similar to that of amino acids 75 to 1371 of NP_620596 (ADAMTS13 isoform 2, mature polypeptide; e.g., residues 75-1371 of SEQ ID NO: 2). In yet another embodiment, ADAMTS13 proteins include polypeptides comprising an amino acid sequence highly similar to that of NP 620595 (ADAMTS13 isoform 3, preproprotein; e.g., SEQ ID NO: 3) or amino acids 75 to 1340 of NP_620595 (ADAMTS13 isoform 3, mature polypeptide; e.g., residues 75-1340 of SEQ ID NO: 3).

In some embodiments of any of the aspects, the ADAMTS13 protein comprises one of SEQ ID NOs: 1-3 or a functional fragment thereof that maintains the same function. In some embodiments of any of the aspects, the ADAMTS13 protein comprises an amino acid sequence that is at least at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% identical to one of SEQ ID NOs: 1-3 or a functional fragment thereof that maintains the same function. In some embodiments of any of the aspects, the ADAMTS13 protein comprises an amino acid sequence that is at least at least 95% identical to one of SEQ ID NOs: 1-3 or a functional fragment thereof (e.g., residues 75-1427 of SEQ ID NO: 1, residues 75-1371 of SEQ ID NO: 2, or residues 75-1340 of SEQ ID NO: 3) that maintains the same function.

> SEQ ID NO: 1, ADAMTS13 isoform 1 preproprotein [*Homo sapiens*] NCBI Reference Sequence: NP_620594.1, 1427 amino acids (aa)
> SEQ ID NO: 2, ADAMTS13 isoform 2 preproprotein [*Homo sapiens*] NCBI Reference Sequence: NP_620596.2, 1371 aa
> SEQ ID NO: 3, ADAMTS13 isoform 3 preproprotein [*Homo sapiens*] NCBI Reference Sequence: NP_620595.1, 1340 aa In certain aspects, an ADAMTS13 protein includes natural variants with VWF cleaving activity and artificial constructs with VWF cleaving activity. In certain aspects, ADAMTS13 encompasses any natural variants, alternative sequences, isoforms or mutant proteins that retain some basal activity. Many natural variants of human ADAMTS13 are known in the art, and are embraced by the formulations of the disclosure, some of which include mutations selected from R7W, V88M, H96D, R102C, R193W, T196I, H234Q, A250V, R268P, W390C, R398H, Q448E, Q456H, P457L, P475S, C508Y, R528G, P618A, R625H, I673F, R692C, A732V, E740K, A900V, S903L, C908Y, C951G, G982R, C1024G, A1033T, R1095W, R1095W, R1123C, C1213Y, T12261, G1239V, and R1336W. Additionally, ADAMTS13 proteins include natural and recombinant proteins that have been mutated, for example, by one or more conservative mutations at a non-essential amino acid. Preferably, amino acids essential to the enzymatic activity of ADAMTS13 will not be mutated. These include, for example, residues known or presumed to be essential for metal binding such as residues 83, 173, 224, 228, 234, 281, and 284, and residues found in the active site of the enzyme, e.g., residue 225. Similarly, in the context of the disclosure, ADAMTS13 proteins include alternate isoforms, for example, isoforms lacking amino acids 275 to 305 (e.g., Isoform 3) and/or 1135 to 1190 (e.g., Isoforms 2 and 3) of the full-length human protein.

In some aspects, ADAMTS13 proteins are further modified, for example, by post-translational modifications (e.g., glycosylation at one or more amino acids selected from human residues 142, 146, 552, 579, 614, 667, 707, 828, 1235, 1354, or any other natural or engineered modification site) or by ex vivo chemical or enzymatic modification, including without limitation, glycosylation, modification by water-soluble polymer (e.g., PEGylation, sialylation, HESylation, etc.), tagging, and the like.

In some aspects, the ADAMTS13 protein is human ADAMTS13 or a biologically active derivative or fragment thereof as described in U.S. Patent Application Publication No. 2011/0229455 and/or in U.S. Patent Application Publication No. 2014/0271611, each of which are incorporated herein by reference in their entirety and for all purposes.

In certain aspects, the recombinant ADAMTS13 can be BAX930/SHP655/TAK755. BAX930/SHP655/TAK755 is a fully glycosylated recombinant human ADAMTS13 protein (see e.g., WO2002042441, which is incorporated herein by reference in its entirety). In certain aspects, the ADAMTS13 protein includes any protein or polypeptide with ADAMTS13 activity, particularly the ability to cleave the peptide bond between residues Tyr-842 and Met-843 of VWF with at least 70%, at least 75%, at least 80%, at least 85%, at least 90%, at least 91%, at least 92%, at least 93%, at least 94%, at least 95%, at least 96%, at least 97%, at least 98%, or at least 99% sequence homology to BAX930/SHP655/TAK755.

Proteolytically active recombinant ADAMTS13 may be prepared by expression in mammalian cell cultures, as described in Plaimauer et al., (2002, Blood. 15; 100(10): 3626-32) and US 2005/0266528, the disclosures of which are herein incorporated by reference in their entireties for all purposes. Methods for the expression of recombinant ADAMTS13 in cell culture are disclosed in Plaimauer B, Scheiflinger F. (Semin Hematol. 2004 January; 41(1):24-33 and US 2011/0086413, the disclosures of which are herein incorporated by reference in their entireties for all purposes. See also, WO2012/006594, incorporated by reference in their entireties for all purposes, for methods of producing recombinant ADAMTS13 in cell culture.

Methods for purifying ADAMTS13 protein from a sample are described in U.S. Pat. No. 8,945,895, which is incorporated herein by reference for all purposes. Such methods include, in some aspects, enriching for ADAMTS13 protein by chromatographically contacting the sample with hydroxyapatite under conditions that allow ADAMTS13 protein to appear in the eluate or supernatant from the hydroxyapatite. The methods may further comprise tandem chromatography with a mixed mode cation exchange/hydrophobic interaction resin that binds ADAMTS13 protein. Additional optional steps involve ultrafiltration/diafiltration, anion exchange chromatography, cation exchange chromatography, and viral inactivation. In some aspects, such methods include inactivating virus contaminants in protein samples, where the protein is immobilized on a support. Also provided herein, in some aspects, are compositions of ADAMTS13 prepared according to the methods described in U.S. Pat. No. 8,945,895.

ADAMTS13 Compositions and Administration

In aspects of the disclosure, ADAMTS13 is administered to a subject in need thereof. To administer ADAMTS13 described herein to a subject, ADAMTS13 is, in some aspects, formulated in a composition comprising one or more pharmaceutically acceptable carriers.

The term "pharmaceutically acceptable," as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans. "Pharmaceutically acceptable carriers" include any and all clinically useful solvents, dispersion media, coatings, antibacterial and antifungal agents, isotonic and absorption delaying agents and the like. In some aspects, the composition forms solvates with water or common organic solvents. Such solvates are included as well.

In some aspects, the disclosure provides stabilized formulations of plasma derived ADAMTS13 and recombinant ADAMTS13 (rADAMTS13) proteins as described in U.S. Pat. No. 8,623,352 and/or in U.S. Patent Application Publication No. 2014/0271611, both of which are incorporated herein by reference for all purposes. In some embodiments, the formulations provided herein retain significant ADAMTS13 activity when stored for extended periods of time. In some embodiments, the formulations of the disclosure reduce or retard dimerization, oligomerization, and/or aggregation of an ADAMTS13 protein.

In some aspects, the disclosure provides formulations of ADAMTS13 comprising a therapeutically effective amount or dose of an ADAMTS13 protein, a sub-physiological to physiological concentration of a pharmaceutically acceptable salt, a stabilizing concentration of one or more sugars and/or sugar alcohols, a non-ionic surfactant, a buffering agent providing a neutral pH to the formulation, and optionally a calcium and/or zinc salt. Generally, the stabilized ADAMTS13 formulations provided herein are suitable for pharmaceutical administration. In some aspects, the ADAMTS13 protein is human ADAMTS13 or a biologically active derivative or fragment thereof as described in U.S. Patent Application Publication No. 2011/0229455 and/or in U.S. Patent Application Publication No. 2014/0271611, each of which are incorporated herein by reference in their entirety and for all purposes.

In some aspects, the ADAMTS13 formulations are liquid or lyophilized formulations. In other embodiments, a lyophilized formulation is lyophilized from a liquid formulation as described in U.S. Patent Application Publication No. 2011/0229455 and/or in U.S. Patent Application Publication No. 2014/0271611, each of which are incorporated herein by reference in their entirety and for all purposes. In certain embodiments of the formulations provided herein, the ADAMTS13 protein is a human ADAMTS13 or recombinant human ADAMTS13, or a biologically active derivative or fragment thereof as described in U.S. Patent Application Publication No. 2011/0229455 and/or in U.S. Patent Application Publication No. 2014/0271611, each of which are incorporated herein by reference in their entirety and for all purposes.

The composition of the disclosure is, in various aspects, administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. In some embodiments, administration is subcutaneous. Administration by intravenous, intradermal, intramuscular, intramammary, intraperitoneal, intrathecal, retrobulbar, intrapulmonary injection and or surgical implantation at a particular site is contemplated as well. In some embodiments, administration is intravenous. Generally, compositions are essentially free of pyrogens, as well as other impurities that could be harmful to the recipient.

Formulation of the composition or pharmaceutical composition will vary according to the route of administration selected (e.g., solution or emulsion). An appropriate composition comprising the composition to be administered is prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles, in some aspects, include sodium chloride solution, Ringer's dextrose, dextrose and sodium chloride, lactated Ringer's or fixed oils. Intravenous vehicles, in certain aspects, include various additives, preservatives, or fluid, nutrient or electrolyte replenishers.

Compositions or pharmaceutical compositions useful in the compounds and methods of the disclosure containing ADAMTS13 as an active ingredient contain, in various aspects, pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form.

A variety of aqueous carriers, e.g., water, buffered water, 0.4% saline, 0.3% glycine, or aqueous suspensions contain, in various aspects, the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents, in some instances, are a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions, in some aspects, contain one or more preservatives, for example ethyl, or n-propyl, p-hydroxybenzoate.

In some aspects, ADAMTS13 or ADAMTS13 compositions are lyophilized for storage and reconstituted in a suitable carrier prior to use. Any suitable lyophilization and reconstitution techniques known in the art are employed. It is appreciated by those skilled in the art that lyophilization and reconstitution leads to varying degrees of protein activity loss and that use levels are often adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

In some embodiments, the ADAMTS13 formulations provided herein may further comprise one or more pharmaceutically acceptable excipients, carriers, and/or diluents as described in U.S. Patent Application Publication No. 2011/0229455 and/or in U.S. Patent Application Publication No. 2014/0271611, each of which are incorporated herein by reference in their entirety and for all purposes.

In some embodiments, the ADAMTS13 formulations provided herein will have a tonicity in a range described in as described in U.S. Patent Application Publication No.

2011/0229455 and/or in U.S. Patent Application Publication No. 2014/0271611, each of which are incorporated herein by reference in their entirety and for all purposes.

In some aspects, the disclosure provides formulations of ADAMTS13 comprising the exemplary formulations described in Section III ("ADAMTS13 Compositions and Formulations") of U.S. Patent Application Publication No. 2011/0229455. The methods of ADAMTS13 production and compositions thereof as described in U.S. Patent Application Publication No. 2011/0229455 and/or in U.S. Patent Application Publication No. 2014/0271611 are incorporated herein by reference in their entirety for all purposes. Additionally, actual methods for preparing parenterally administrable formulations and compositions are known or are apparent to those skilled in the art and are described in more detail in, for example, Remington's Pharmaceutical Science, 15th ed., Mack Publishing Company, Easton, Pa. (1980).

In various aspects, the pharmaceutical compositions are in the form of a sterile injectable aqueous, oleaginous suspension, dispersions or sterile powders for the extemporaneous preparation of sterile injectable solutions or dispersions. The suspension, in some aspects, is formulated according to the known art using those suitable dispersing or wetting agents and suspending agents which have been mentioned above. The sterile injectable preparation, in certain aspects, is a sterile injectable solution or suspension in a non-toxic parenterally-acceptable diluent or solvent, for example as a solution in 1,3-butane diol. In some embodiments, the carrier is a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil is employed, in various aspects, including synthetic mono- or diglycerides. In addition, fatty acids such as oleic acid find use in the preparation of injectables.

In all cases the form must be sterile and must be fluid to the extent that easy syringeability exists. The proper fluidity is maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms is brought about by various antibacterial and antifungal agents, for example, parabens, chlorobutanol, phenol, sorbic acid, thimerosal, and the like. In many cases, it will be desirable to include isotonic agents, for example, sugars or sodium chloride. In certain aspects, prolonged absorption of the injectable compositions is brought about by the use in the compositions of agents delaying absorption, for example, aluminum monostearate and gelatin.

Compositions useful for administration, in certain aspects, are formulated with uptake or absorption enhancers to increase their efficacy. Such enhancers include, for example, salicylate, glycocholate/linoleate, glycholate, aprotinin, bacitracin, SDS, caprate and the like. See, e.g., Fix (J. Pharm. Sci., 85:1282-1285, 1996) and Oliyai et al. (Ann. Rev. Pharmacol. Toxicol., 32:521-544, 1993), each of which are incorporated herein by reference in their entirety and for all purposes.

In addition, the properties of hydrophilicity and hydrophobicity of the compositions used in the compositions and methods of the disclosure are well balanced, thereby enhancing their utility for both in vitro and especially in vivo uses, while other compositions lacking such balance are of substantially less utility. Specifically, compositions in the disclosure have an appropriate degree of solubility in aqueous media which permits absorption and bioavailability in the body, while also having a degree of solubility in lipids which permits the compounds to traverse the cell membrane to a putative site of action.

In particular aspects, ADAMTS13 is provided in a pharmaceutically acceptable (i.e., sterile and non-toxic) liquid, semisolid, or solid diluent that serves as a pharmaceutical vehicle, excipient, or medium. Any diluent known in the art is used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

The composition is packaged in forms convenient for delivery. The composition is enclosed within a capsule, caplet, sachet, cachet, gelatin, paper, or other container. These delivery forms are preferred when compatible with delivery of the composition into the recipient organism and, particularly, when the composition is being delivered in unit dose form. The dosage units are packaged, e.g., in vials, tablets, capsules, suppositories, or cachets.

The disclosure includes methods for treating, ameliorating, and/or preventing graft rejection and/or increasing graft survival in a subject, including administering an effective amount of ADAMTS13 or an ADAMTS13 composition as described herein. The composition is introduced into the subject to be treated by any conventional method as described herein in detail above. In certain aspects, the composition is administered in a single dose or a plurality of doses over a period of time (as described in more detail below).

In some embodiments, the composition comprising ADAMTS13 and/or additional treatments are administered to the subject within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 60, 72, 84, 96, 108, or 120 hours after transplant or the onset of the of graft rejection. In some embodiments, the composition comprising ADAMTS13 is administered to the subject within about 1-2 hours, about 1-5 hours, about 1-10 hours, about 1-12 hours, about 1-24 hours, about 1-36 hours, about 1-48 hour, about 1-60 hours, about 1-72 hours, about 1-84 hours, about 1-96 hours, about 1-108 hours, or about 1-120 hours after transplant or the onset of the of graft rejection. In some embodiments, the composition comprising ADAMTS13 is administered to the subject within about 2-5 hours, about 5-10 hours, about 10-20 hours, about 20-40 hours, about 30-60 hours, about 40-80 hours, about 50-100 hours, or about 60-120 hours after transplant or the onset of the of graft rejection. In some embodiments, the composition is administered within 1 week of after transplant or the onset of the of graft rejection. In some embodiments, the composition is administered daily after transplant or the onset of the of graft rejection. In some embodiments, the composition is administered weekly after transplant or the onset of the of graft rejection. In some embodiments, the composition is administered every day. In some embodiments, the composition is administered every other day. In some embodiments, the composition is administered every third day. In some embodiments, the composition is administered twice a week. In some embodiments, the composition is administered until the clinical manifestations (e.g., symptoms and/or biomarkers) resolve. In some embodiments, the composition is administered until a day after clinical manifestations resolve. In some embodiments, the composition is administered for at least two days after clinical manifestations resolve. In some embodiments, the composition is administered for at least three days after clinical manifestations resolve. In some embodiments, the composition is administered for at least a week after clinical manifestations resolve.

In some aspects, the composition comprising ADAMTS13 and/or additional treatments is administered to the subject after transplant or the onset of the of graft rejection. In such preventative treatment, ADAMTS13 is administered in a singular bolus injection or in multiple doses to maintain a circulating level of ADAMTS13 effective after transplant or the onset of the of graft rejection. In such aspects, the composition comprising ADAMTS13 is administered monthly, every two weeks, weekly, twice a week, every other day, or daily. In particular aspects, the injection is administered subcutaneously. In other aspects, the injection is administered intravenously.

In some embodiments, the composition comprising ADAMTS13 is administered to the subject before the onset of the graft rejection to prevent the graft rejection. In such aspects of the disclosure, the composition is administered in a therapeutically effective amount or dose sufficient to maintain an effective level of ADAMTS13 activity in the subject or in the blood of the subject.

Dosing of ADAMTS13 Compositions/Methods of Treating

In various aspects, the effective dosage of ADAMTS13 or an ADAMTS13 composition to be administered varies depending on multiple factors which modify the action of drugs, e.g. the age, condition, body weight, sex, and diet of the subject, the severity of any infection, time of administration, mode of administration, and other clinical factors, including the severity of the graft rejection.

In some aspects, formulations or compositions of the disclosure are administered by an initial bolus followed by booster delivery after a period of time has elapsed. In certain aspects, formulations of the disclosure are administered by an initial bolus followed by a continuous infusion to maintain therapeutic circulating levels of ADAMTS13. In particular aspects, ADAMTS13 or an ADAMTS13 composition of the disclosure is administered over extended periods of time. In some aspects, the ADAMTS13 or ADAMTS13 composition is delivered in a rapid treatment regimen to relieve acute symptoms of graft rejection. In some aspects, the ADAMTS13 or ADAMTS13 composition is delivered in a prolonged and varied treatment regimen to prevent the occurrence of graft rejection. As another example, the composition or formulation of the disclosure is administered as a one-time dose. Those of ordinary skill in the art readily optimize effective dosages and administration regimens as determined by good medical practice and the clinical condition of the individual subject. The frequency of dosing depends on the pharmacokinetic parameters of the agents, the route of administration, and the condition of the subject.

The pharmaceutical formulation is determined by one skilled in the art depending upon the route of administration and desired dosage. See for example, Remington's Pharmaceutical Sciences, 18th Ed. (1990, Mack Publishing Co., Easton, PA 18042) pages 1435-1712, the disclosure of which is hereby incorporated by reference for all purposes. Such formulations, in some instances, influence the physical state, stability, rate of in vivo release, and rate of in vivo clearance of the administered composition. Depending on the route of administration, a suitable dose is calculated, in particular aspects, according to body weight, body surface area or organ size. In some aspects, appropriate dosages are ascertained through use of established assays for determining blood level dosages in conjunction with appropriate dose-response data. In certain aspects, the antibody titer of an individual is measured to determine optimal dosage and administration regimens. The final dosage regimen will be determined by the attending doctor or physician, considering various factors which modify the action of the pharmaceutical compositions, e.g. the composition's specific activity, the responsiveness of the subject, the age, condition, body weight, sex and diet of the subject, the severity of any infection or malignant condition, time of administration and other clinical factors, including the severity of the pain or the graft rejection.

In certain aspects, the ADAMTS13 or ADAMTS13 composition comprises any dose of ADAMTS13 sufficient to evoke a response in the subject. In some embodiments, the dose of ADAMTS13 is sufficient to treat graft rejection. In some embodiments, the dose of ADAMTS13 is sufficient to prevent graft rejection. The effective amount of ADAMTS13 or ADAMTS13 composition to be employed therapeutically will depend, for example, upon the therapeutic context and objectives. One skilled in the art will appreciate that the appropriate dosage levels for treatment or prevention will thus vary depending, in part, upon the molecule delivered, the indication for which the ADAMTS13 or ADAMTS13 composition is being used, the route of administration, and the size (e.g., body weight, body surface or organ size) and condition (e.g., the age and general health) of the patient. Accordingly, the clinician, in some instances, titers the dosage and modifies the route of administration to obtain the optimal therapeutic effect.

Dosage, unless otherwise specifically recited, is provided in international units. As discussed herein below, the use of international units (IU) is the new standard for measuring ADAMTS13 activity. Up until recently, FRETS units (or FRETS-VWF73 test units) were the standard for measuring ADAMTS13 activity. 20 FRETS units (FRETS U) is equivalent to approximately 21.78 IU. In other words, 20 IU of ADAMTS13 is equivalent to about 18.22 FRETS U of ADAMTS13.

A typical dosage, in various aspects, ranges from about 10 international units per kilogram body weight up to about 10,000 international units per kilogram body weight. In some aspects, a dosage or therapeutically effective amount of ADAMTS13 is up to about 10,000 international units per kilogram body weight or more, depending on the factors mentioned above. In other aspects, the dosage may range from about 20 to about 6,000 international units per kilogram body weight. In some aspects, the dosage or therapeutically effective amount of ADAMTS13 is from about 40 to about 4,000 international units per kilogram body weight. In some aspects, the dosage or therapeutically effective amount is from about 100 to about 3,000 international units per kilogram body weight.

In particular aspects, the dosage or therapeutically effective amount is from about 10 to about 500 international units per kilogram body weight. In some aspects, the dosage or therapeutically effective amount is from about 50 to about 450 international units per kilogram body weight. In some aspects, the therapeutically effective amount is from about 40 to about 100 international units per kilogram body weight. In some aspects, the therapeutically effective amount is from about 40 to about 150 international units per kilogram body weight. In some aspects, the dosage or therapeutically effective amount is from about 100 to about 500 international units per kilogram body weight. In some aspects, the dosage or therapeutically effective amount is from about 100 to about 400 international units per kilogram body weight. In some aspects, the dosage or therapeutically effective amount is from about 100 to about 300 international units per kilogram body weight. In some aspects, the dosage or therapeutically effective amount is from about 300 to about 500 international units per kilogram body weight. In some aspects, the dosage or therapeutically effective amount is from about 200 to about 300 international units per kilogram body weight. In some aspects, the dosage or therapeutically effective amount is about 100, about 150, about 200, about 250, about 300, about 350, about 400, about 450, or about 500 international units per kilogram body weight.

In further aspects, the dosage or therapeutically effective amount is from about 50 to about 1,000 international units per kilogram body weight. In some aspects, the dosage or therapeutically effective amount is from about 100 to about 900 international units per kilogram body weight. In some aspects, the dosage or therapeutically effective amount is from about 200 to about 800 international units per kilogram body weight. In some aspects, the dosage or therapeutically effective amount is from about 300 to about 700 international units per kilogram body weight. In some aspects, the dosage or therapeutically effective amount is from about 400 to about 600 international units per kilogram body weight. In some aspects, the dosage or therapeutically effective amount is about 500 international units per kilogram body weight.

In some aspects, the dosage or therapeutically effective amount is about 10 international units per kilogram body weight, about 20 international units per kilogram body weight, about 30 international units per kilogram body weight, about 40 international units per kilogram body weight, about 50 international units per kilogram body weight, about 60 international units per kilogram body weight, about 70 international units per kilogram body weight, about 80 international units per kilogram body weight, about 90 international units per kilogram body weight, about 100 international units per kilogram body weight, about 120 international units per kilogram body weight, about 140 international units per kilogram body weight, about 150 international units per kilogram body weight, about 160 international units per kilogram body weight, about 180 international units per kilogram body weight, about 200 international units per kilogram body weight, about 220 international units per kilogram body weight, about 240 international units per kilogram body weight, about 250 international units per kilogram body weight, about 260 international units per kilogram body weight, about 280 international units per kilogram body weight, about 300 international units per kilogram body weight, about 350 international units per kilogram body weight, about 400 international units per kilogram body weight, about 450 international units per kilogram body weight, about 500 international units per kilogram body weight, about 550 international units per kilogram body weight, about 600 international units per kilogram body weight, about 650 international units per kilogram body weight, about 700 international units per kilogram body weight, about 750 international units per kilogram body weight, about 800 international units per kilogram body weight, about 850 international units per kilogram body weight, about 900 international units per kilogram body weight, about 950 international units per kilogram body weight, about 1,000 international units per kilogram body weight, about 1,100 international units per kilogram body weight, about 1,100 international units per kilogram body weight, about 1,200 international units per kilogram body weight, about 1,300 international units per kilogram body weight, about 1,400 international units per kilogram body weight, about 1,500 international units per kilogram body weight, about 1,600 international units per kilogram body weight, about 1,800 international units per kilogram body weight, about 2,000 international units per kilogram body weight, about 2,500 international units per kilogram body weight, about 3,000 international units per kilogram body weight, about 3,500 international units per kilogram body weight, about 4,000 international units per kilogram body weight, about 4,500 international units per kilogram body weight, about 5,000 international units per kilogram body weight, about 5,500 international units per kilogram body weight, about 6,000 international units per kilogram body weight, about 6,500 international units per kilogram body weight, about 7,000 international units per kilogram body weight, about 7,500 international units per kilogram body weight, about 8,000 international units per kilogram body weight, about 8,500 international units per kilogram body weight, about 9,000 international units per kilogram body weight, about 9,500 international units per kilogram body weight, and about 10,000 international units per kilogram body weight.

As used herein, "one unit of ADAMTS13 activity" or "one activity unit" is defined as the amount of activity in 1 mL of pooled normal human plasma, regardless of the assay being used. As provided above, however, the new standard for measuring or dosing ADAMTS13 is international units (IU). 20 FRETS test units or 20 FRETS units (FRETS U) is equivalent to approximately 21.78 IU. In other words, 20 IU of ADAMTS13 is equivalent to about 18.22 FRETS U of ADAMTS13. Thus, the change to the new standard results in an approximate shift of 8.9% in the conversion of FRETS U to IU.

In some aspects, fluorescence resonance energy transfer (FRET) assays are used to measure ADAMTS13 activity. FRET requires two interacting partners of which one is labeled with a donor fluorophore and the other is labeled with an acceptor fluorophore. FRET assays for ADAMTS13 involve a chemically modified fragment of the A2 domain of VWF which spans the ADAMTS13 cleavage site. This is readily cleaved by normal plasma but not by ADAMTS13 deficient plasma. This cleavage is blocked by EDTA and so samples for this assay must be collected into tubes that contain citrate as an anticoagulant and not EDTA. One unit of ADAMTS13 FRETS-VWF73 activity is the amount of activity needed to cleave the same amount of FRETS-VWF73 substrate (Kokame et al., Br J. Haematol. 2005 April; 129(1):93-100, incorporated herein by reference in its entirety) as is cleaved by one mL of pooled normal human plasma.

In some aspects, additional activity assays are used for measuring the activity of ADAMTS13. For example, direct ADAMTS13 activity assays can be performed to detect the cleavage of either full-length VWF molecules or VWF fragments using SDS agarose gel electrophoresis and indirect detection of ADAMTS13 activity can be detected with collagen binding assays. Direct assays, including the FRET assay, as described herein, involve the detection of cleavage of products either of a full-length VWF molecule or a VWF fragment that encompasses the ADAMTS13 cleavage site. With SDS agarose gel electrophoresis and Western Blotting, purified VWF is incubated with plasma for 24 hours. Cleavage of the VWF by ADAMTS13 takes place leading to a reduction in multimer sizes. This reduction is visualized by agarose gel electrophoresis followed by Western blotting with a peroxidase-conjugated anti-VWF antibody. The concentration of ADAMTS13 activity in the test sample can be established by reference to a series of diluted normal plasma samples. SDS-PAGE and Western Blotting can also be carried out, which involves the visualization of dimeric VWF fragments following SDS PAGE and Western Blotting. The assay is technically easier than SDS agarose gel electrophoresis and appears a very sensitive method for measuring ADAMTS13 activity levels.

In some aspects, indirect assays involve the detection of cleavage of products either of a full-length VWF molecule or a VWF fragment that encompasses the ADAMTS13 cleavage site in the A2 domain of VWF. Such assays include collagen binding assays, where normal plasma or purified VWF is incubated with the test plasma sample in the presence of $BaCl_2$ and 1.5M urea which denatures the VWF. VWF is cleaved by ADAMTS13 and residual VWF is measured by its binding to collagen Type III. The bound VWF is quantitated using an ELISA assay with a conjugated anti-VWF antibody. Another indirect assay is the ristocetin-induced aggregation assay. This is similar to the collagen-binding assay above but residual VWF is measured by ristocetin-induced platelet aggregation using a platelet aggregometer. Another indirect assay is a functional ELISA. In this assay, a recombinant VWF fragment is immobilized onto an ELISA plate using an antibody to a tag on the VWF. The VWF fragment encodes the A2 domain and the ADAMTS13 cleavage site at Tyr1605-Met1606 and is tagged with S-transferase [GST]-histidine [GST-VWF73-His]. Plasma is added to the immobilized GST-VWF73-His fragment and cleavage of the immobilized fragment occurs at the ADAMTS13 cleavage site. The residual, cleaved VWF fragment is measured by using a second monoclonal antibody that recognizes only the cleaved VWF fragment and NOT the intact fragment. ADAMTS13 activity is, therefore, inversely proportional to the residual substrate concentration.

ADAMTS13 activity may be assessed by ADAMTS13 functional assays (see e.g., Peyvandi et al., J Thromb Haemost; 8: 631-40, 2010). Exemplary functional assays may use full-length VWF under moderate denaturing conditions (e.g., in the presence of urea or guanidine hydrochloride) to unfold the VWF substrate and to make it susceptible for ADAMTS13 cleavage, or utilize short peptidyl substrates (such as the VWF73 substrate) (Kokame et al., Blood; 103(2): 607-12, 2004; Kokame et al., Br J Haematol; 129(1): 93-100, 2005; each of which are herein incorporated by reference in its entirety). Such small peptide substrates are derived from the A2 domain of VWF and contain the minimal VWF amino acid region required to be recognized and cleaved by ADAMTS13 as substrate (Kokame et al., Br J Haematol; 129(1): 93-100, 2005, which is incorporated herein by reference in its entirety).

In certain embodiments, a flow-based assay (see e.g., Han et al., Transfusion; 51(7): 1580-91, 2011, which is incorporated herein by reference in its entirety) is used to assess ADAMTS13 activity. The assay mimics the in vivo physiologic flow conditions necessary to achieve conformational changes of the full-length VWF substrate required for ADAMTS13 binding and ADAMTS13-mediated cleavage (Shim et al., Blood; 111(2): 651-7, 2008, which is incorporated herein by reference in its entirety).

In certain embodiments, ADAMTS13 is provided or administered in a therapeutically effective concentration between about 0.05 mg/mL and about 10 mg/mL in the final formulation. In other embodiments, ADAMTS13 is present at a concentration of between about 0.1 mg/mL and about 10 mg/mL. In yet other embodiments, ADAMTS13 is present at a concentration of between about 0.1 mg/mL and about 5 mg/mL. In another embodiment, ADAMTS13 is present at a concentration of between about 0.1 mg/mL and about 2 mg/mL. In yet other embodiments, ADAMTS13 may be present at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration.

In some embodiments, the concentration of a relatively pure ADAMTS13 formulation may be determined by spectroscopy (i.e., total protein measured at A280) or other bulk determination (e.g., Bradford assay, silver stain, weight of a lyophilized powder, etc.). In other embodiments, the concentration of ADAMTS13 may be determined by an ADAMTS13 ELISA assay (e.g., mg/mL antigen).

In some aspects, the concentration of ADAMTS13 in a formulation of the disclosure is expressed as a level of enzymatic activity. For example, in some embodiments, an ADAMTS13 formulation contains between about 10 units of FRETS-VWF73 activity and about 10,000 units of FRETS-VWF73 activity or other suitable ADAMTS13 enzymatic unit (IU). In other embodiments, the formulation may contain between about 20 units of FRETS-VWF73 ($U_{FV73}$) activity and about 8,000 units of FRETS-VWF73 activity, or between about 30 $U_{FV73}$ and about 6,000 $U_{FV73}$, or between about 40 $U_{FV73}$ and about 4,000 $U_{FV73}$, or between about 50 $U_{FV73}$ and about 3,000 $U_{FV73}$, or between about 75 $U_{FV73}$ and about 2,500 $U_{FV73}$, or between about 100 $U_{FV73}$ and about 2,000 $U_{FV73}$, or between about 200 $U_{FV73}$ and about 1,500 $U_{FV73}$, or between about other ranges therein.

In some embodiments, ADAMTS13 is provided or administered at a dose of from about 10 $U_{FV73}$/kg body weight to 10,000 $U_{FV73}$/kg body weight. In one embodiment, ADAMTS13 is administered at a dose of from about 20 $U_{FV73}$/kg body weight to about 8,000 $U_{FV73}$/kg body weight. In one embodiment, ADAMTS13 is administered at a dose of from about 30 $U_{FV73}$/kg body weight to about 6,000 $U_{FV73}$/kg body weight. In one embodiment, ADAMTS13 is administered at a dose of from about 40 $U_{FV73}$/kg body weight to about 4,000 $U_{FV73}$/kg body weight. In one embodiment, ADAMTS13 is administered at a dose of from about 100 $U_{FV73}$/kg body weight to about 3,000 $U_{FV73}$/kg body weight. In one embodiment, ADAMTS13 is administered at a dose of from about 200 $U_{FV73}$/kg body weight to about 2,000 $U_{FV73}$/kg body weight. In other embodiments, ADAMTS13 is administered at about 10 $U_{FV73}$/kg body weight, about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,500, 5,000, 5,500, 6,000, 6,500, 7,000, 7,500, 8,000, 8,500, 9,000, 9,500, or 10,000 $U_{FV73}$/kg body weight, or at an intermediate dose or dose range thereof.

In some aspects, an ADAMTS13 formulation provided herein contains between about 20 and about 10,000 $U_{FV}$73.

In some embodiments, a formulation contains about 10 units of FRETS-VWF73 activity, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more units of FRETS-VWF73 activity.

In some aspects, the concentration of ADAMTS13 may be expressed as an enzymatic activity per unit volume, for example, ADAMTS13 enzymatic units per mL (IU/mL). For example, in some embodiments, an ADAMTS13 formulation contains between about 10 IU/mL and about 10,000 IU/mL. In some other embodiments, the formulation contains between about 20 IU/mL and about 10,000 IU/mL, or between about 20 IU/mL and about 8,000 IU/mL, or between about 30 IU/mL and about 6,000 IU/mL, or between about 40 IU/mL and about 4,000 IU/mL, or between about 50 IU/mL and about 3,000 IU/mL, or between about 75 IU/mL and about 2,500 IU/mL, or between about 100 IU/mL and about 2,000 IU/mL, or between about 200 IU/mL and about 1,500 IU/mL, or between about other ranges therein. In some embodiments, an ADAMTS13 formulation provided herein contains between about 150 IU/mL and about 600 IU/mL. In another embodiment, an ADAMTS13 formulation provided herein contains between about 100 IU/mL and about 1,000 IU/mL. In some embodiments, an ADAMTS13 formulation provided herein contains between about 100 IU/mL and about 800 IU/mL. In some embodiments, an ADAMTS13 formulation provided herein contains between about 100 IU/mL and about 600 IU/mL. In some embodiments, an ADAMTS13 formulation provided herein contains between about 100 IU/mL and about 500 IU/mL. In some embodiments, an ADAMTS13 formulation provided herein contains between about 100 IU/mL and about 400 IU/mL. In some embodiments, an ADAMTS13 formulation provided herein contains between about 100 IU/mL and about 300 IU/mL. In some embodiments, an ADAMTS13 formulation provided herein contains between about 100 IU/mL and about 200 IU/mL. In some embodiments, an ADAMTS13 formulation provided herein contains between about 300 IU/mL and about 500 IU/mL. In some embodiments, an ADAMTS13 formulation provided herein contains about 100 IU/mL. In some embodiments, an ADAMTS13 formulation provided herein contains about 300 IU/mL. In various embodiments, a formulation contains about 10 IU/mL, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more IU/mL.

In some embodiments, administering ADAMTS13 or a composition comprising ADAMTS13 results in a desired plasma ADAMTS13 concentration. The plasma ADAMTS13 concentration may be determined after a certain period of time (e.g., 5 minutes, 1 hour, 3 hours or 24 hours) post administration. In some embodiments, administering ADAMTS13 or a composition comprising ADAMTS13 results a plasma ADAMTS13 concentration of about 0.5 to about 100 U/mL in the subject. For example, in some embodiments, administering ADAMTS13 or a composition comprising ADAMTS13 results in a plasma ADAMTS13 concentration of about 1 to about 80 U/mL in the subject. In some embodiments, administering ADAMTS13 or a composition comprising ADAMTS13 results in a plasma ADAMTS13 concentration of about 5 to about 50 U/mL in the subject. In some embodiments, administering ADAMTS13 or a composition comprising ADAMTS13 results in a plasma ADAMTS13 concentration of about 12 to about 50 U/mL in the subject. In some embodiments, administering ADAMTS13 or a composition comprising ADAMTS13 results in a plasma ADAMTS13 concentration of about 5 to about 20 U/mL in the subject.

In some embodiments, administering ADAMTS13 or a composition comprising ADAMTS13 results in a plasma ADAMTS13 concentration of about 1 U/mL, about 2 U/mL, about 3 U/mL, about 4 U/mL, about 5 U/mL, about 6 U/mL, about 7 U/mL, about 8 U/mL, about 9 U/mL, about 10 U/mL, about 11 U/mL, about 12 U/mL, about 13 U/mL, about 14 U/mL, about 15 U/mL, about 16 U/mL, about 17 U/mL, about 18 U/mL, about 19 U/mL, about 20 U/mL, about 21 U/mL, about 22 U/mL, about 22 U/mL, about 23 U/mL, about 24 U/mL, about 25 U/mL, about 26 U/mL, about 27 U/mL, about 28 U/mL, about 29 U/mL, about 30 U/mL, about 32 U/mL, about 34 U/mL, about 36 U/mL, about 38 U/mL, about 40 U/mL, about 42 U/mL, about 44 U/mL, about 46 U/mL, about 48 U/mL, about 50 U/mL, about 52 U/mL, about 54 U/mL, about 56 U/mL, about 58 U/mL, about 60 U/mL, about 70 U/mL, about 80 U/mL, or more than 80 U/mL in the subject.

In some embodiments, the ADAMTS13 formulations provided herein may further comprise one or more pharmaceutically acceptable excipients, carriers, and/or diluents as described in U.S. Patent Application Publication No. 2011/0229455 and/or in U.S. Patent Application Publication No. 2014/0271611, each of which incorporated by reference in their entirety for all purposes. Furthermore, in one embodiment, the ADAMTS13 formulations provided herein will have a tonicity in a range described in as described in U.S. Patent Application Publication No. 2011/0229455 and/or in U.S. Patent Application Publication No. 2014/0271611, each of which incorporated by reference in their entirety for all purposes.

The frequency of dosing will depend upon the pharmacokinetic parameters of the ADAMTS13 molecule in the formulation used. Typically, a clinician will administer the composition until a dosage is reached that achieves the desired effect. The composition, in various aspects, is therefore administered as a single dose, or as two or more doses (which may or may not contain the same amount of the desired molecule) over time, or as a continuous infusion via an implantation device or catheter. In some aspects, the composition comprising ADAMTS13 is administered in a single bolus injection, monthly, every two weeks, weekly, twice a week, every other day, daily, every 12 hours, every eight hours, every six hours, every four hours, or every two hours. In the prophylactic or preventative treatment aspects of the disclosure, ADAMTS13 is administered in multiple doses to maintain a circulating level of ADAMTS13 effective to prevent the onset of the graft rejection. In such aspects, the composition comprising ADAMTS13 is administered monthly, every two weeks, weekly, twice a week, every other day, or daily. In particular aspects, the injection is administered subcutaneously (e.g., WO2014151968, incorporated herein by reference in its entirety for all purposes). In other aspects, the injection is administered intravenously. Further refinement of the appropriate dosage administered and the timing of administration is routinely made by those of ordinary skill in the art and is within the ambit of tasks routinely performed by them. Appropriate dosages are often ascertained through use of appropriate dose-response data which is routinely obtained.

Kits Comprising ADAMTS13

As an additional aspect, the disclosure includes kits which comprise one or more pharmaceutical formulations for administration of ADAMTS13 or an ADAMTS13 composition to a subject packaged in a manner which facilitates their use for administration to the subject.

In a specific embodiment, the disclosure includes kits for producing a single dose administration unit. In another embodiment, the disclosure includes kits for providing multiple dose administration units. The kits, in various aspects, each contain both a first container having a dried protein and a second container having an aqueous formulation. Also included within the scope of this disclosure are kits containing single and multi-chambered pre-filled syringes (e.g., liquid syringes and lyosyringes).

In another embodiment, such a kit includes a pharmaceutical formulation described herein (e.g., a composition comprising a therapeutic protein, e.g., ADAMTS13), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none).

In some aspects, the pharmaceutical formulation or composition comprises a stabilizer. The term "stabilizer" refers to a substance or excipient which protects the composition from adverse conditions, such as those which occur during heating or freezing, and/or prolongs the stability or shelf-life of the composition or pharmaceutical composition in a stable state. Examples of stabilizers include, but are not limited to, sugars, such as sucrose, lactose and mannose; sugar alcohols, such as mannitol; amino acids, such as glycine or glutamic acid; and proteins, such as human serum albumin or gelatin.

In some aspects, the pharmaceutical formulation or composition comprises an antimicrobial preservative. The term "antimicrobial preservative" refers to any substance which is added to the composition that inhibits the growth of microorganisms that may be introduced upon repeated puncture of multidose vials, should such containers be used. Examples of antimicrobial preservatives include, but are not limited to, substances such as thimerosal, 2-phenoxyethanol, benzethonium chloride, and phenol.

In one aspect, the kit contains a first container having a therapeutic protein or protein composition and a second container having a physiologically acceptable reconstitution solution for the composition. In one aspect, the pharmaceutical formulation is packaged in a unit dosage form. The kit optionally further includes a device suitable for administering the pharmaceutical formulation according to a specific route of administration. In some aspects, the kit contains a label that describes use of the pharmaceutical formulations.

In one aspect, the kit comprises at least one reagent for detecting the level of one or more genes or gene products, selected from the group consisting of: PAD4, H3Cit, H4Cit, MPO, NE, and NLRP3. In one aspect, the kit comprises at least one reagent for detecting the level of histone modifications, cell-free DNA, H3Cit, H4Cit, NE and/or MPO-DNA conjugates.

This entire document is intended to be related as a unified disclosure, and it should be understood that all combinations of features described herein are contemplated, even if the combination of features are not found together in the same sentence, or paragraph, or section of this document. The disclosure also includes, for instance, all embodiments of the disclosure narrower in scope in any way than the variations specifically mentioned above.

All publications, patents and patent applications cited in this specification are herein incorporated by reference as if each individual publication or patent application were specifically and individually indicated to be incorporated by reference in its entirety to the extent that it is not inconsistent with the disclosure.

It is understood that the examples and embodiments described herein are for illustrative purposes only and that various modifications or changes in light thereof will be suggested to persons skilled in the art and are to be included within the spirit and purview of this application and scope of the appended claims.

Treatment Methods

In one aspect described herein is a method for treating or preventing graft rejection in a subject that received a graft, the method comprising administering to the subject in need thereof a therapeutically effective amount of a composition comprising A Disintegrin And Metalloproteinase with Thrombospondin type 1 motif, member-13 (ADAMTS13). In another aspect described herein is the use of a composition comprising ADAMTS13 and a carrier for treating or preventing graft rejection in a subject that received a graft. In another aspect described herein is a composition comprising ADAMTS13 and a carrier for use as a medicament for the treatment or prevention of graft rejection in a subject that received a graft.

In another aspect described herein is a method for increasing graft survival in a subject that received a graft, the method comprising administering to the subject in need thereof a therapeutically effective amount of a composition comprising A Disintegrin And Metalloproteinase with Thrombospondin type 1 motif, member-13 (ADAMTS13). In another aspect described herein is the use of a composition comprising ADAMTS13 and a carrier for increasing graft survival in a subject that received a graft. In another aspect described herein is a composition comprising ADAMTS13 and a carrier for use as a medicament for increasing graft survival in a subject that received a graft.

In some embodiments of any of the aspects, the subject is administered ADAMTS13 after at least one symptom of graft rejection is present. In some embodiments of any of the aspects, the subject is administered ADAMTS13 before a symptom of graft rejection is present.

In some embodiments of any of the aspects, administering ADAMTS13 reduces and/or prevents at least one of graft deterioration, graft desiccation, graft shrinkage, scab formation, graft hardening, loss of hair, graft dysfunction, organ deterioration, organ damage, organ dysfunction, cell damage, inflammation, swelling, erythema, seroma, severity of pain, infection, NET burden, neutrophil recruitment, lymphocyte recruitment, platelet aggregation, microthrombosis, generation of inappropriate angiogenesis or a combination of any thereof as compared to control, the subject without treatment, and/or the subject before transplantation. In some embodiments of any of the aspects, the lymphocyte recruitment is T-cell recruitment. In some embodiments of any of the aspects, there is a reduction and/or prevention in NET burden.

In some embodiments of any of the aspects, administering ADAMTS13 results in at least one of increased survival of the graft, improved organ function, increased survival of the subject, or a combination of any thereof as compared to control, the subject without treatment, and/or the subject before transplantation.

In some embodiments of any of the aspects, the therapeutically effective amount of ADAMTS13 is from about 20 to about 6,000 international units per kilogram body weight. In some embodiments of any of the aspects, the therapeutically effective amount of ADAMTS13 is from about 40 to about 4,000 international units per kilogram body weight. In some embodiments of any of the aspects, the therapeutically effective amount of ADAMTS13 is from about 100 to about 3,000 international units per kilogram body weight. In some embodiments of any of the aspects, the therapeutically effective amount of ADAMTS13 is from about 50 to about 500 international units per kilogram body weight.

In some embodiments of any of the aspects, the composition comprising ADAMTS13 is administered in a single bolus injection, monthly, every two weeks, weekly, twice a week, daily, every 12 hours, every eight hours, every six hours, every four hours, or every two hours. In some embodiments of any of the aspects, the composition comprising ADAMTS13 is administered intravenously, subcutaneously, or dermally.

In some embodiments of any of the aspects, the ADAMTS13 is recombinant ADAMTS13. In some embodiments of any of the aspects, the ADAMTS13 is plasma derived.

In some embodiments of any of the aspects, the subject is a mammal. In some embodiments of any of the aspects, the subject is a human.

In some embodiments of any of the aspects, the composition is in a stable aqueous solution ready for administration.

In some embodiments of any of the aspects, the therapeutically effective amount of the composition comprising ADAMTS13 is administered to the subject within 48 hours after receiving the graft. In some embodiments of any of the aspects, the therapeutically effective amount of the composition comprising ADAMTS13 is sufficient to maintain an effective level of ADAMTS13 activity in the subject.

In some embodiments of any of the aspects, the graft is an allograft. In some embodiments of any of the aspects, the graft is an autograft. In some embodiments of any of the aspects, the graft is an isograft. In some embodiments of any of the aspects, the graft is a xenograft. In some embodiments of any of the aspects, the xenograft is obtained from a pig, a primate, or a cow. In some embodiments of any of the aspects, the graft is an artificially manufactured device. In some embodiments of any of the aspects, the graft is a skin, cells, bone, nerves, tendons, neurons, blood vessels, fat, or cornea graft. In some embodiments of any of the aspects, the graft is transplanted to the subject suffering from a wound, a burn, a damaged organ, or an infection, and/or a subject that has undergone surgery.

In some embodiments of any of the aspects, the method further comprises modifying one or more additional genes or gene products such that the expression and/or function of said additional gene(s) or gene product(s) is reduced or eliminated, wherein said additional gene(s) or gene product(s) are PAD4, H3Cit, H4Cit, MPO, NE, or NLRP3.

In some embodiments of any of the aspects, the modifying of one or more additional genes comprises disrupting said gene(s) with a site-specific nuclease. In some embodiments of any of the aspects, the site-specific nuclease comprises a Cas protein and a guide RNA. In some embodiments of any of the aspects, the Cas protein is a Cas9 protein. In some embodiments of any of the aspects, the guide RNA is a single guide RNA (sgRNA). In some embodiments of any of the aspects, the site-specific nuclease comprises a zinc finger nuclease (ZFN), a TALEN nuclease, or a mega-TALEN nuclease.

In some embodiments of any of the aspects, the modifying of one or more additional gene products comprises administering an RNA interference (RNAi) molecule or an antisense oligonucleotide. In some embodiments of any of the aspects, the RNAi molecule is a small interfering RNA (siRNA) or a small hairpin RNA (shRNA).

In some embodiments of any of the aspects, the modifying of one or more additional gene products comprises administering one or more of a small molecule inhibitor, a peptide, an antibody or antibody fragment, and an aptamer.

In some embodiments of any of the aspects, the method further comprises inhibiting NET formation and/or neutrophil infiltration. In some embodiments of any of the aspects, the inhibiting NET formation comprises administering one or more of a small molecule inhibitor, a peptide, an antibody or antibody fragment, and an aptamer. In some embodiments of any of the aspects, the inhibiting of NET formation is by administering, increasing the expression of, and/or activating DNase 1.

Methods of Determining the Likelihood that a Graft Will Be Rejected

In one aspect described herein is a method for determining the likelihood that a graft will be rejected by a subject, the method comprising: (a) determining the level of NET and/or PAD4 in the graft, or a CSF or a blood sample obtained from the subject before the graft is transplanted, (b) determining the level of NET and/or PAD4 in the graft, or the CSF or a blood sample obtained from the subject after the graft is transplanted, (c) comparing the levels determined in steps (a) and (b), and (d) determining that the subject is at risk for rejecting the graft if the level of NET and/or PAD4 in the graft, or the CSF or the blood of the subject has increased after the graft is transplanted as compared to a control.

In another aspect described herein is a method for determining the likelihood that a graft will be rejected by a subject, the method comprising: (a) determining the level of NET and/or PAD4 in the graft, or a CSF or a blood sample obtained from the subject after the graft is transplanted, (b) determining the level of NET and/or PAD4 in the same tissue as the graft in step (a), or the CSF or a blood sample obtained from a control, (c) comparing the levels determined in steps (a) and (b), and (d) determining that the subject is at risk for rejecting the graft if the level of NET and/or PAD4 in the graft, or the CSF or the blood of the subject is higher in the graft as compared to a control.

In some embodiments of any of the aspects, the control is a predetermined standard, or a healthy age- and gender-matched subject, or an average value for several such subjects. In some embodiments of any of the aspects, the control or reference level can be the level in a sample of similar cell type, sample type, sample processing, and/or obtained from a subject of similar age, sex and other demographic parameters as the sample/subject. In some embodiments, the test sample and control reference sample are of the same type, that is, obtained from the same biological source, and comprising the same composition, e.g. the same number and type of cells.

In some embodiments of any of the aspects, the level of NET is determined by measuring the levels of histone modifications, cell-free DNA, H3Cit, H4Cit, NE and/or MPO-DNA conjugates. In some embodiments of any of the aspects, the level of PAD4 is determined by measuring the levels of PAD4 gene expression, PAD4 protein expression, histone modifications, H3Cit, H4Cit, and/or MPO. In some embodiments of any of the aspects, the levels are determined using a method selected from hybridization, array-based assays, PCR-based assays, and sequencing.

In some embodiments of any of the aspects, the method further comprises administering ADAMTS13 or a composition comprising ADAMTS13, as described further herein. In some embodiments of any of the aspects, the method further comprises administering ADAMTS13 or a composition comprising ADAMTS13, after step (d) of determining that the subject is at risk for rejecting the graft if the level of NET and/or PAD4 in the graft, or the CSF or the blood of the subject has increased after the graft is transplanted as compared to a control. In some embodiments of any of the aspects, it is determined that the subject is not at risk for rejecting the graft if the level of NET and/or PAD4 in the graft, or the CSF or the blood of the subject has not increased after the graft is transplanted as compared to a control. In some embodiments of any of the aspects, if it is determined that the subject is not at risk for rejecting the graft, then ADAMTS13 or a composition comprising ADAMTS13 is not administered, or a lower dose of ADAMTS13 or a composition comprising ADAMTS13 is administered compared to when the subject is at risk for rejecting the graft, or an alternative treatment is administered.

In some embodiments of any of the aspects, the method further comprises modifying one or more additional genes or gene products such that the expression and/or function of said additional gene(s) or gene product(s) is reduced or eliminated, wherein said additional gene(s) or gene product(s) are PAD4, H3Cit, H4Cit, MPO, NE, or NLRP3. In some embodiments of any of the aspects, the method further comprises modifying one or more additional genes or gene products, after step (d) of determining that the subject is at risk for rejecting the graft if the level of NET and/or PAD4 in the graft, or the CSF or the blood of the subject has increased after the graft is transplanted as compared to a control. In some embodiments of any of the aspects, it is determined that the subject is not at risk for rejecting the graft if the level of NET and/or PAD4 in the graft, or the CSF or the blood of the subject has not increased after the graft is transplanted as compared to a control. In some embodiments of any of the aspects, if it is determined that the subject is not at risk for rejecting the graft, then one or more additional genes or gene products are not modified, or fewer additional genes or gene products are modified compared to when the subject is at risk for rejecting the graft, or an alternative treatment is administered.

In some embodiments of any of the aspects, the method further comprises inhibiting NET formation and/or neutrophil infiltration. In some embodiments of any of the aspects, the inhibiting NET formation comprises administering one or more of a small molecule inhibitor, a peptide, an antibody or antibody fragment, and an aptamer. In some embodiments of any of the aspects, the inhibiting of NET formation is by administering, increasing the expression of, and/or activating DNase 1. In some embodiments of any of the aspects, the DNase 1 that is administered comprises an effective dose of Dornase alfa (Genentech™) using an effective administration route.

In some embodiments of any of the aspects, the method further comprises inhibiting NET formation and/or neutrophil infiltration, after step (d) of determining that the subject is at risk for rejecting the graft if the level of NET and/or PAD4 in the graft, or the CSF or the blood of the subject has increased after the graft is transplanted as compared to a control. In some embodiments of any of the aspects, it is determined that the subject is not at risk for rejecting the graft if the level of NET and/or PAD4 in the graft, or the CSF or the blood of the subject has not increased after the graft is transplanted as compared to a control. In some embodiments of any of the aspects, if it is determined that the subject is not at risk for rejecting the graft, then NET formation and/or neutrophil infiltration is not inhibited, or NET formation and/or neutrophil infiltration is inhibited less than compared to when the subject is at risk for rejecting the graft, or an alternative treatment is administered.

As described herein, levels of NET and/or PAD4 can be increased in graft rejection and/or in subjects with graft rejection. Accordingly, in one aspect of any of the embodiments, described herein is a method of treating graft rejection in a subject in need thereof, the method comprising administering an ADAMTS13 composition as described herein to a subject determined to have a level of NET and/or PAD4 that is increased relative to a reference. In one aspect of any of the embodiments, described herein is a method of treating graft rejection in a subject in need thereof, the method comprising: a) determining the level of NET and/or PAD4 in a sample obtained from a subject; and b) administering an ADAMTS13 composition as described herein to the subject if the level of NET and/or PAD4 is increased relative to a reference.

In some embodiments of any of the aspects, the method comprises administering an ADAMTS13 composition as described herein to a subject previously determined to have a level of NET and/or PAD4 that is increased relative to a reference. In some embodiments of any of the aspects, described herein is a method of treating graft rejection in a subject in need thereof, the method comprising: a) first determining the level of NET and/or PAD4 in a sample obtained from a subject; and b) then administering an ADAMTS13 composition as described herein to the subject if the level of NET and/or PAD4 is increased relative to a reference.

In one aspect of any of the embodiments, described herein is a method of treating graft rejection in a subject in need thereof, the method comprising: a) determining if the subject has an increased level of NET and/or PAD4; and b) administering an ADAMTS13 composition as described herein to the subject if the level of NET and/or PAD4 is increased relative to a reference. In some embodiments of any of the aspects, the step of determining if the subject has an increased level of NET and/or PAD4 can comprise i) obtaining or having obtained a sample from the subject and ii) performing or having performed an assay on the sample obtained from the subject to determine/measure the level of NET and/or PAD4 in the subject. In some embodiments of any of the aspects, the step of determining if the subject has an increased level of NET and/or PAD4 can comprise performing or having performed an assay on a sample obtained from the subject to determine/measure the level of NET and/or PAD4 in the subject. In some embodiments of any of the aspects, the step of determining if the subject has an increased level of NET and/or PAD4 can comprise ordering or requesting an assay on a sample obtained from the subject to determine/measure the level of NET and/or PAD4 in the subject. In some embodiments of any of the aspects, the step of determining if the subject has an increased level of NET and/or PAD4 can comprise receiving the results of an assay on a sample obtained from the subject to determine/measure the level of NET and/or PAD4 in the subject. In some embodiments of any of the aspects, the step of determining if the subject has an increased level of NET and/or PAD4 can comprise receiving a report, results, or other means of identifying the subject as a subject with an increased level of NET and/or PAD4.

In one aspect of any of the embodiments, described herein is a method of treating graft rejection in a subject in need thereof, the method comprising: a) determining if the subject has an increased level of NET and/or PAD4; and b) instructing or directing that the subject be administered an ADAMTS13 composition as described herein if the level of NET and/or PAD4 is increased relative to a reference. In some embodiments of any of the aspects, the step of determining if the subject has an increased level of NET and/or PAD4 can comprise i) obtaining or having obtained a sample from the subject and ii) performing or having performed an assay on the sample obtained from the subject to determine/measure the level of NET and/or PAD4 in the subject. In some embodiments of any of the aspects, the step of determining if the subject has an increased level of NET and/or PAD4 can comprise performing or having performed an assay on a sample obtained from the subject to determine/measure the level of NET and/or PAD4 in the subject. In some embodiments of any of the aspects, the step of determining if the subject has an increased level of NET and/or PAD4 can comprise ordering or requesting an assay on a sample obtained from the subject to determine/measure the level of NET and/or PAD4 in the subject. In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

Some embodiments of the technology described herein can be defined according to any of the following numbered paragraphs:

1. A method for treating or preventing graft rejection in a subject that received a graft, the method comprising administering to the subject in need thereof a therapeutically effective amount of a composition comprising A Disintegrin And Metalloproteinase with Thrombospondin type 1 motif, member-13 (ADAMTS13).

2. The method of paragraph 1, wherein the subject is administered ADAMTS13 after at least one symptom of graft rejection is present.

3. The method of paragraph 1, wherein the subject is administered ADAMTS13 before a symptom of graft rejection is present.

4. The method of any one of paragraphs 1-3, wherein administering ADAMTS13 reduces and/or prevents at least one of graft deterioration, graft desiccation, graft shrinkage, scab formation, graft hardening, loss of hair, graft dysfunction, organ deterioration, organ damage, organ dysfunction, cell damage, inflammation, swelling, erythema, seroma, severity of pain, infection, NET burden, neutrophil recruitment, lymphocyte recruitment, platelet aggregation, microthrombosis, generation of inappropriate angiogenesis or a combination of any thereof as compared to control, the subject without treatment, and/or the subject before transplantation.

5. The method of paragraph 4, wherein the lymphocyte recruitment is T-cell recruitment.

6. The method of paragraph 4 or paragraph 5, wherein there is a reduction and/or prevention in NET burden.

7. The method of any one of paragraphs 1-6, wherein administering ADAMTS13 results in at least one of increased survival of the graft, improved organ function, increased survival of the subject, or a combination of any thereof as compared to control, the subject without treatment, and/or the subject before transplantation.

8. The method of any one of paragraphs 1-7, wherein the therapeutically effective amount of ADAMTS13 is from about 20 to about 6,000 international units per kilogram body weight.

9. The method of any one of paragraphs 1-8, wherein the therapeutically effective amount of ADAMTS13 is from about 40 to about 4,000 international units per kilogram body weight.

10. The method of any one of paragraphs 1-9, wherein the therapeutically effective amount of ADAMTS13 is from about 100 to about 3,000 international units per kilogram body weight.

11. The method of any one of paragraphs 1-10, wherein the therapeutically effective amount of ADAMTS13 is from about 50 to about 500 international units per kilogram body weight.

12. The method of any one of paragraphs 1-11, wherein the composition comprising ADAMTS13 is administered in a single bolus injection, monthly, every two weeks, weekly, twice a week, daily, every 12 hours, every eight hours, every six hours, every four hours, or every two hours.

13. The method of any one of paragraphs 1-12, wherein the composition comprising ADAMTS13 is administered intravenously, subcutaneously, or dermally.

14. The method of any one of paragraphs 1-13, wherein the ADAMTS13 is recombinant ADAMTS13.

15. The method of any one of paragraphs 1-13, wherein the ADAMTS13 is plasma derived.

16. The method of any one of paragraphs 1-15, wherein the subject is a mammal.

17. The method of any one of paragraphs 1-16, wherein the subject is a human.

18. The method of any one of paragraphs 1-17, wherein the composition is in a stable aqueous solution ready for administration.

19. The method of any one of paragraphs 1-18, wherein the therapeutically effective amount of the composition comprising ADAMTS13 is administered to the subject within 48 hours after receiving the graft.

20. The method of any one of paragraphs 1-19, wherein the therapeutically effective amount of the composition comprising ADAMTS13 is sufficient to maintain an effective level of ADAMTS13 activity in the subject.

21. The method of any one paragraphs 1-20, wherein the graft is an allograft.

22. The method of any one paragraphs 1-20, wherein the graft is an autograft.

23. The method of any one paragraphs 1-20, wherein the graft is an isograft

24. The method of any one paragraphs 1-20, wherein the graft is a xenograft.

25. The method of paragraph 24, wherein the xenograft is obtained from a pig, a primate, or a cow.

26. The method of any one paragraphs 1-20, wherein the graft is an artificially manufactured device.

27. The method of any one of paragraphs 1-22, wherein the graft is a skin, cells, bone, nerves, tendons, neurons, blood vessels, fat, or cornea graft.

28. The method of any one of paragraphs 1-27, wherein the graft is transplanted to the subject suffering from a wound, a burn, a damaged organ, or an infection, and/or a subject that has undergone surgery.

29. The method of any one of paragraphs 1-28, further comprising modifying one or more additional genes or gene products such that the expression and/or function of said additional gene(s) or gene product(s) is reduced or eliminated, wherein said additional gene(s) or gene product(s) are PAD4, H3Cit, H4Cit, MPO, NE, or NLRP3.

30. The method of paragraph 29, wherein the modifying of one or more additional genes comprises disrupting said gene(s) with a site-specific nuclease.

31. The method of paragraph 30, wherein the site-specific nuclease comprises a Cas protein and a guide RNA.

32. The method of paragraph 31, wherein the Cas protein is a Cas9 protein.

33. The method of paragraph 31 or paragraph 32, wherein the guide RNA is a single guide RNA (sgRNA).

34. The method of paragraph 30, wherein the site-specific nuclease comprises a zinc finger nuclease (ZFN), a TALEN nuclease, or a mega-TALEN nuclease.

35. The method of paragraph 29, wherein the modifying of one or more additional gene products comprises administering an RNA interference (RNAi) molecule or an antisense oligonucleotide.

36. The method of paragraph 35, wherein the RNAi molecule is a small interfering RNA (siRNA) or a small hairpin RNA (shRNA).

37. The method of paragraph 29, wherein the modifying of one or more additional gene products comprises administering one or more of a small molecule inhibitor, a peptide, an antibody or antibody fragment, and an aptamer.

38. The method of any one of paragraphs 1-37, further comprising inhibiting NET formation and/or neutrophil infiltration.

39. The method of paragraph 38, wherein the inhibiting NET formation comprises administering one or more of a small molecule inhibitor, a peptide, an antibody or antibody fragment, and an aptamer.

40. The method of paragraph 39, wherein the inhibiting of NET formation is by administering, increasing the expression of, and/or activating DNase 1.

41. Use of a composition comprising ADAMTS13 and a carrier for treating or preventing graft rejection in a subject that received a graft.

42. A composition comprising ADAMTS13 and a carrier for use as a medicament for the treatment or prevention of graft rejection in a subject that received a graft.

43. A method for increasing graft survival in a subject that received a graft, the method comprising administering to the subject in need thereof a therapeutically effective amount of a composition comprising A Disintegrin And Metalloproteinase with Thrombospondin type 1 motif, member-13 (ADAMTS13).

44. The method of paragraph 43, wherein the subject is administered ADAMTS13 after at least one symptom of graft rejection is present.

45. The method of paragraph 43, wherein the subject is administered ADAMTS13 before a symptom of graft rejection is present.

46. The method of any one of paragraphs 43-45, wherein administering ADAMTS13 reduces and/or prevents at least one of graft deterioration, graft desiccation, graft shrinkage, scab formation, graft hardening, loss of hair, graft dysfunction, organ deterioration, organ damage, organ dysfunction, cell damage, inflammation, swelling, erythema, seroma, severity of pain, infection, NET burden, neutrophil recruitment, lymphocyte recruitment, platelet aggregation, microthrombosis, generation of inappropriate angiogenesis or a combination of any thereof as compared to control, the subject without treatment, and/or the subject before transplantation.

47. The method of paragraph 46, wherein the lymphocyte recruitment is T-cell recruitment.

48. The method of paragraph 46 or paragraph 47, wherein there is a reduction and/or prevention in NET burden.

49. The method of any one of paragraphs 43-48, wherein the therapeutically effective amount of ADAMTS13 is from about 20 to about 6,000 international units per kilogram body weight.

50. The method of any one of paragraphs 43-49, wherein the therapeutically effective amount of ADAMTS13 is from about 40 to about 4,000 international units per kilogram body weight.

51. The method of any one of paragraphs 43-50, wherein the therapeutically effective amount of ADAMTS13 is from about 100 to about 3,000 international units per kilogram body weight.

52. The method of any one of paragraphs 43-51, wherein the therapeutically effective amount of ADAMTS13 is from about 50 to about 500 international units per kilogram body weight.

53. The method of any one of paragraphs 43-52, wherein the composition comprising ADAMTS13 is administered in a single bolus injection, monthly, every two weeks, weekly, twice a week, daily, every 12 hours, every eight hours, every six hours, every four hours, or every two hours.

54. The method of any one of paragraphs 43-53, wherein the composition comprising ADAMTS13 is administered intravenously, subcutaneously, or dermally.

55. The method of any one of paragraphs 43-54, wherein the ADAMTS13 is recombinant ADAMTS13.

56. The method of any one of paragraphs 43-55, wherein the ADAMTS13 is plasma derived.

57. The method of any one of paragraphs 43-56, wherein the subject is a mammal.

58. The method of any one of paragraphs 43-57, wherein the subject is a human.

59. The method of any one of paragraphs 43-58, wherein the composition is in a stable aqueous solution ready for administration.

60. The method of any one of paragraphs 43-59, wherein the therapeutically effective amount of the composition comprising ADAMTS13 is administered to the subject within 48 hours after receiving the graft.

61. The method of any one of paragraphs 43-60, wherein the therapeutically effective amount of the composition comprising ADAMTS13 is sufficient to maintain an effective level of ADAMTS13 activity in the subject.

62. The method of any one paragraphs 43-61, wherein the graft is an allograft.

63. The method of any one paragraphs 43-61, wherein the graft is an autograft.

64. The method of any one paragraphs 43-61, wherein the graft is an isograft

65. The method of any one paragraphs 43-61, wherein the graft is a xenograft.

66. The method of paragraph 65, wherein the xenograft is obtained from a pig, a primate, or a cow.

67. The method of any one paragraphs 43-66, wherein the graft is an artificially manufactured device.

68. The method of any one of paragraphs 43-67, wherein the graft is a skin, cells, bone, nerves, tendons, neurons, blood vessels, fat, or cornea graft.

69. The method of any one of paragraphs 43-68, wherein the graft is transplanted to the subject suffering from a wound, a burn, a damaged organ, or an infection, and/or a subject that has undergone surgery.

70. The method of any one of paragraphs 43-69, further comprising modifying one or more additional genes or gene products such that the expression and/or function of said additional gene(s) or gene product(s) is reduced or eliminated, wherein said additional gene(s) or gene product(s) are PAD4, H3Cit, H4Cit, MPO, NE, or NLRP3.

71. The method of paragraph 70, wherein the modifying of one or more additional genes comprises disrupting said gene(s) with a site-specific nuclease.

72. The method of paragraph 71, wherein the site-specific nuclease comprises a Cas protein and a guide RNA.

73. The method of paragraph 72, wherein the Cas protein is a Cas9 protein.

74. The method of paragraph 72 or paragraph 73, wherein the guide RNA is a single guide RNA (sgRNA).

75. The method of paragraph 71, wherein the site-specific nuclease comprises a zinc finger nuclease (ZFN), a TALEN nuclease, or a mega-TALEN nuclease.

76. The method of paragraph 71, wherein the modifying of one or more additional gene products comprises administering an RNA interference (RNAi) molecule or an antisense oligonucleotide.

77. The method of paragraph 76, wherein the RNAi molecule is a small interfering RNA (siRNA) or a small hairpin RNA (shRNA).

78. The method of paragraph 71, wherein the modifying of one or more additional gene products comprises administering one or more of a small molecule inhibitor, a peptide, an antibody or antibody fragment, and an aptamer.

79. The method of any one of paragraphs 43-78, further comprising inhibiting NET formation and/or neutrophil infiltration.

80. The method of paragraph 79, wherein the inhibiting NET formation comprises administering one or more of a small molecule inhibitor, a peptide, an antibody or antibody fragment, and an aptamer.

81. The method of paragraph 79, wherein the inhibiting of NET formation is by administering, increasing the expression of, and/or activating DNase 1.

82. Use of a composition comprising ADAMTS13 and a carrier for increasing graft survival in a subject that received a graft.

83. A composition comprising ADAMTS13 and a carrier for use as a medicament for increasing graft survival in a subject that received a graft.

84. A method for determining the likelihood that a graft will be rejected by a subject, the method comprising:
   a. determining the level of NET and/or PAD4 in the graft, or a CSF or a blood sample obtained from the subject before the graft is transplanted,
   b. determining the level of NET and/or PAD4 in the graft, or the CSF or a blood sample obtained from the subject after the graft is transplanted,
   c. comparing the levels determined in steps (a) and (b), and
   d. determining that the subject is at risk for rejecting the graft if the level of NET and/or PAD4 in the graft, or the CSF or the blood of the subject has increased after the graft is transplanted as compared to a control.

85. A method for determining the likelihood that a graft will be rejected by a subject, the method comprising:
   a. determining the level of NET and/or PAD4 in the graft, or a CSF or a blood sample obtained from the subject after the graft is transplanted,
   b. determining the level of NET and/or PAD4 in the same tissue as the graft in step (a), or the CSF or a blood sample obtained from a control,
   c. comparing the levels determined in steps (a) and (b), and
   d. determining that the subject is at risk for rejecting the graft if the level of NET and/or PAD4 in the graft, or the CSF or the blood of the subject is higher in the graft as compared to a control.

86. The method of paragraph 85, wherein the control is a predetermined standard, or a healthy age- and gender-matched subject, or an average value for several such subjects.

87. The method of any one of paragraphs 84-86, wherein the level of NET is determined by measuring the levels of histone modifications, cell-free DNA, H3Cit, H4Cit, NE and/or MPO-DNA conjugates.

88. The method of any one of paragraphs 84-87, wherein the level of PAD4 is determined by measuring the levels of PAD4 gene expression, PAD4 protein expression, histone modifications, H3Cit, H4Cit, and/or MPO.

89. The method of any one of paragraphs 84-88, wherein the levels are determined using a method selected from hybridization, array-based assays, PCR-based assays, and sequencing.

90. The method of any one of paragraphs 84-89, further comprising administering ADAMTS13.

91. The method of paragraph 90, further comprising modifying one or more additional genes or gene products such that the expression and/or function of said additional gene(s) or gene product(s) is reduced or eliminated, wherein said additional gene(s) or gene product(s) are PAD4, H3Cit, H4Cit, MPO, NE, or NLRP3.

92. The method of paragraph 90 or paragraph 91, further comprising inhibiting NET formation and/or neutrophil infiltration.

93. The method of paragraph 92, wherein the inhibiting NET formation comprises administering one or more of a small molecule inhibitor, a peptide, an antibody or antibody fragment, and an aptamer.

94. The method of paragraph 92, wherein the inhibiting of NET formation is by administering, increasing the expression of, and/or activating DNase 1.

EXAMPLES

Additional aspects and details of the disclosure will be apparent from the following examples, which are intended to be illustrative rather than limiting.

Example 1: ADAMTS13 Treatment to Enhance Skin Allograft Survival

Survival of patients suffering severe burn injury is positively correlated to skin allograft tolerance. The objective of this example is to examine the effect of ADAMTS13 treatment and the impact of NETs on skin allografts.

This example utilized a murine model of complete mismatch full thickness skin transplant to demonstrate that NETs are present in the skin allografts of wild-type mouse recipients and burn patients, and that rhADAMTS13 treatment is an anti-NET strategy. This example also shows that PAD4 deficiency or administration of DNase 1 also enhances skin allograft longevity.

1. Materials and Methods 1.1 Animals

All animal procedures were reviewed and approved by an Institutional Animal Care and Use Committee. Male mice aged 8-12 weeks, either bred in-house or purchased from the Jackson Laboratory™, were used in the experiments. Mice were housed individually after skin transplant surgery to prevent them from disturbing grafts of each other. All mice were fed standard lab diet and maintained under standard laboratory conditions free of specific pathogens.

1.2 Skin Transplant Surgery

Complete mismatch skin allograft transplant model was adopted in the present study. BALB/c wild-type (WT) mice were used as skin donors and mice in C57BL/6J background were employed as graft recipients. Donor mice were euthanized by cervical dislocation. Their dorsal skin was rapidly shaved, sterilized alternatively with 70% ethanol wipes and betadine three times, and harvested. Connective tissue, fat tissue, and panniculus *carnosus* were removed from the donor's skin, which was then cut into 1 cm×1 cm grafts and kept in PBS on ice. After graft preparation, the dorsal skin of the recipient mice was shaved and sterilized. With proper anesthesia using isoflurane inhalation, a piece of full thickness skin (1 cm×1 cm) was excised from the back of the recipient mice, followed by suturing of the allograft to the wound. The mice were then bandaged for 7 days, upon which the sutures were removed. Acute graft rejection can begin with e.g., swelling and erythema, followed by e.g., graft desiccation, shrinkage, and scab formation. Complete rejection was defined as complete hardening of the graft with loss of hair.

1.3 Administration of rhADAMTS13 and DNase 1

To examine whether rhADAMTS13 enhances skin allograft survival, BALB/c WT mice were used as skin donors and C57BL/6J WT as allograft recipients. rhAD-AMTS13 (Baxalta/Shire™) was given at 3500 U/kg via retro-orbital intravenous injection immediately after graft-ing, and then once daily up to 7 days post transplantation (see e.g., FIG. 1A). Sterile saline was used as the vehicle control. The experiment was repeated using C57BL/6J *Padi4–/–* mice as allograft recipients.

For DNase 1 treatment, C57BL/6J WT were allograft recipients, and DNase 1 (Dornase Alfa™, Genentech™) was administered at 10 g by retro-orbital intravenous injection 10 min before allograft transplant and 50 g by intraperitoneal injection immediately after the surgery. DNase 1 was then given at 50 g by intraperitoneal injection twice daily for 7 days post-surgery (see e.g., FIG. 2F). Sterile saline was used as the vehicle control.

1.4 Human Specimens

Control skin (i.e., intact skin adjacent to burn wounds or skin collected for autographs) and allografts were procured from burn patients with Institutional Review Board approval and patient consent. The tissues were snap frozen for Western blotting or embedded in optimal cutting temperature compound (OCT) for immunofluorescence staining.

1.5 Immunofluorescence Microscopy

Localization of citrullinated histone H3 or citrullinated histone H4 (H3Cit and H4Cit, NET biomarkers) and neutrophils in the allografts was examined by immunofluorescence microscopy. Human skin and allograft specimens, as well as allografts of vehicle- or rhADAMTS13-treated mice harvested on day 3, were cryosectioned into 10 m sections. The sections were post-fixed in zinc fixative (100 mM Tris-HCl, 37 mM zinc chloride, 23 mM zinc acetate, 3.2 mM calcium acetate), permeabilized with 0.1% Triton-X and 0.1% sodium citrate for 10 min at 4° C., blocked with 3% BSA or 2.5% BSA/5% donkey serum in PBS, and incubated with combinations of primary antibodies against H3Cit (Abcam™, ab5103, 1:1,000), H4Cit (Millipore™, Cat. no. 07-596, 1:250), Ly6G (BD Pharmingen™, Cat. no. 551459, 1:500) or myeloperoxidase (MPO, Abcam™, Cat. no. ab25989, 1:1,000) at 4° C. overnight. After washes, the sections were incubated with appropriate Alexa Fluor-conjugated secondary antibodies (Invitrogen™, 1:1,500) for 2 h at room temperature. Hoechst 33342 (Invitrogen™, Cat. no. H3570, 1:10,000) was used to counterstain for DNA. Images were acquired on an Axiovert™ 200M wide-field fluorescence microscope (Zeiss™) coupled to an AxioCam™ MR3 monochromatic CCD camera (Zeiss™) using a Zeiss Ph2 Neofluar™ 40×/0.75 objective lens with the Zeiss AxioVision™ software (version 4.6.3.0).

1.6 Western Blot Analysis

Levels of H4Cit, MPO and neutrophil elastase of allografts were quantified by Western blotting. Samples were snap frozen upon retrieval, and were homogenized in radio-immunoprecipitation assay (RIPA) buffer supplemented with protease inhibitor cocktails (Sigma™) on ice. After centrifugation at 20,000 g for 20 min at 4° C., the protein content of the supernatant was determined by bicinchoninic acid protein assay and an equal amount of protein per sample was resolved on gradient gels (Bolt™ 4-12% Bis-Tris Plus™ gels, Life Technologies™) and electroblotted on polyvinylidene fluoride (PVDF) membranes. After blocking, the membranes were incubated with primary antibodies against H4Cit (Millipore™, Cat. no. 07-596, 1:500), MPO (DAKO™, A0398, 1:500) or neutrophil elastase (Abcam™, ab68672, 1:500) at 4° C. overnight, and subsequently with goat anti-rabbit IgG (H+L)-HRP (BioRad™, 1:10,000) for 2 h at room temperature. Blots were developed with enhanced chemiluminescence substrate (Thermo Scientific™, Cat. no. 32106). Equal loading was confirmed by probing for glyceraldehyde 3-phosphate dehydrogenase (GAPDH) (Ambion™, Cat. no. AM4300, 1:40,000). Blots were quantified using ImageJ™ software by dividing the intensity of protein-of-interest by the intensity of GAPDH.

1.7 Statistical Analysis

Data are presented as mean S.E.M. At least two independent animal experiments were performed, and were analyzed using Mann-Whitney test or Log-rank test (for graft survival). All analyses were performed using GraphPad Prism™ software (Version 5.0). Results were considered significant when P<0.05. Mice that disturbed or injured their grafts post-surgery were sacrificed immediately and not included.

2. Results 2.1 rhADAMTS13 Treatment Enhances Allograft Survival

Figure 1B:
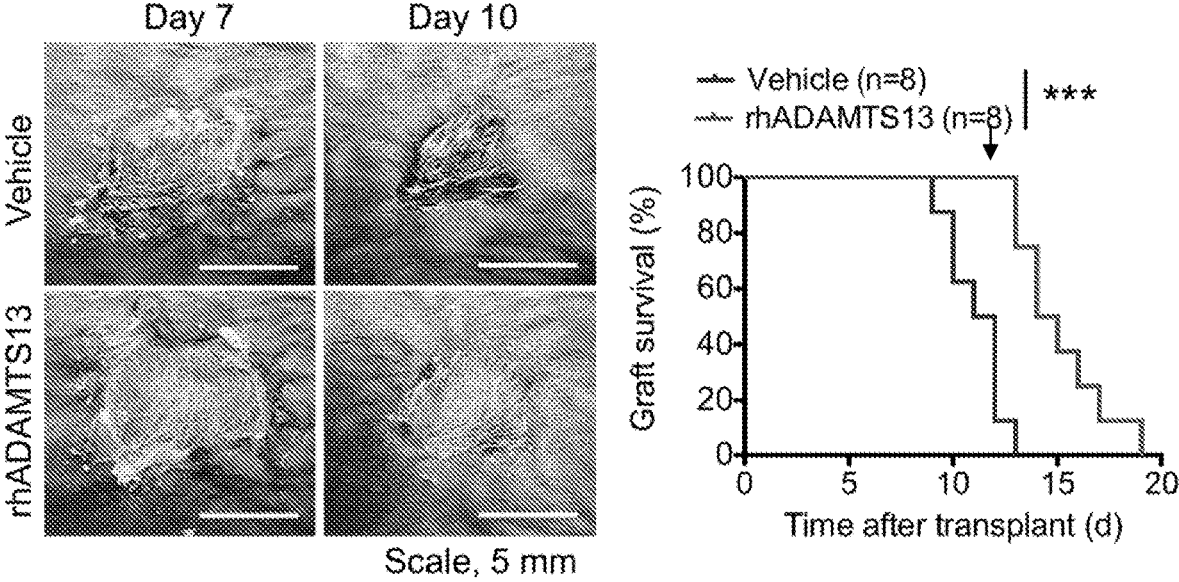

To examine the effect of exogenous ADAMTS13 (i.e., not produced in the mouse) on skin allograft survival, C57BL/6J WT allograft recipients were treated daily with either rhAD-AMTS13 or vehicle for 7 days post-surgery (see e.g., FIG. 1A). The grafts of vehicle- and rhADAMTS13-treated mice were similar in appearance and remained soft on day 7 upon suture removal. Strikingly after this period, the allografts of the vehicle-treated mice showed signs of rejection (e.g., erythema, graft desiccation and shrinkage) much earlier than those of the rhADAMTS13-treated recipients (see e.g., FIG. 1B). Median allograft survivals of vehicle- and rhAD-AMTS13-treated mice were 11.5 and 14.5 days, respectively. rhADAMTS13 was therefore beneficial to allograft survival, and significantly enhanced median survival of the allografts by 26%, compared to the vehicle-treated control.

2.2 NET Burden is Reduced in Allografts of rhADAMTS3-Treated Mice

Figure 1D:
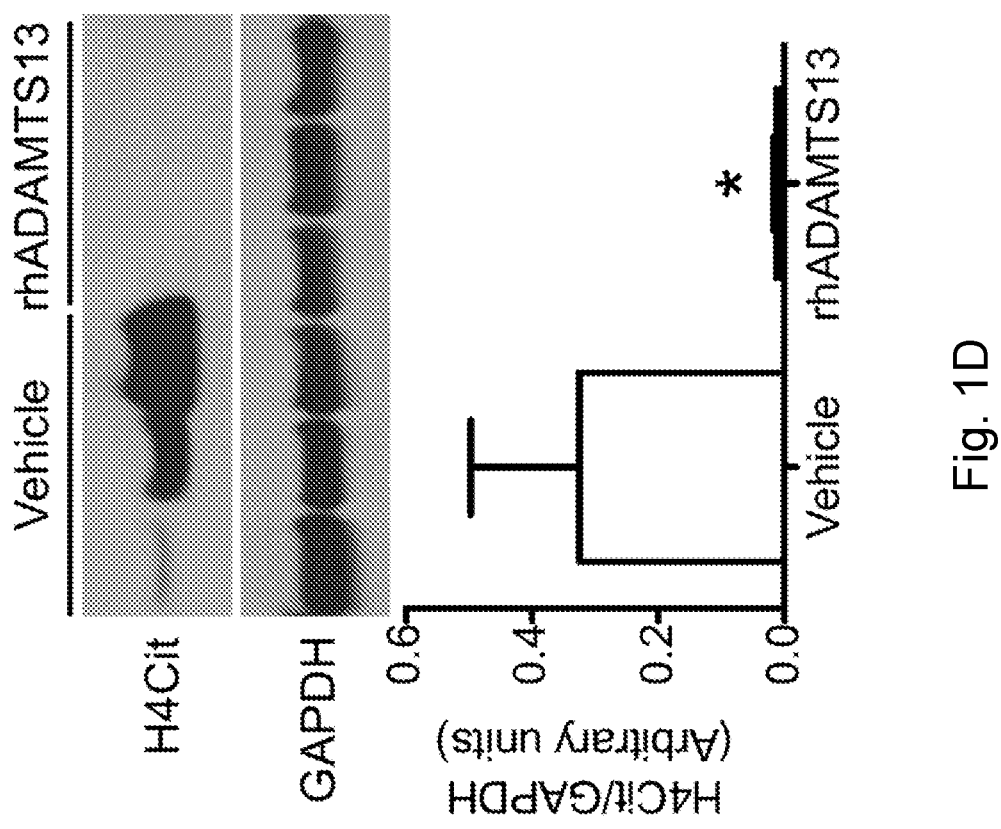
Figure 1C:
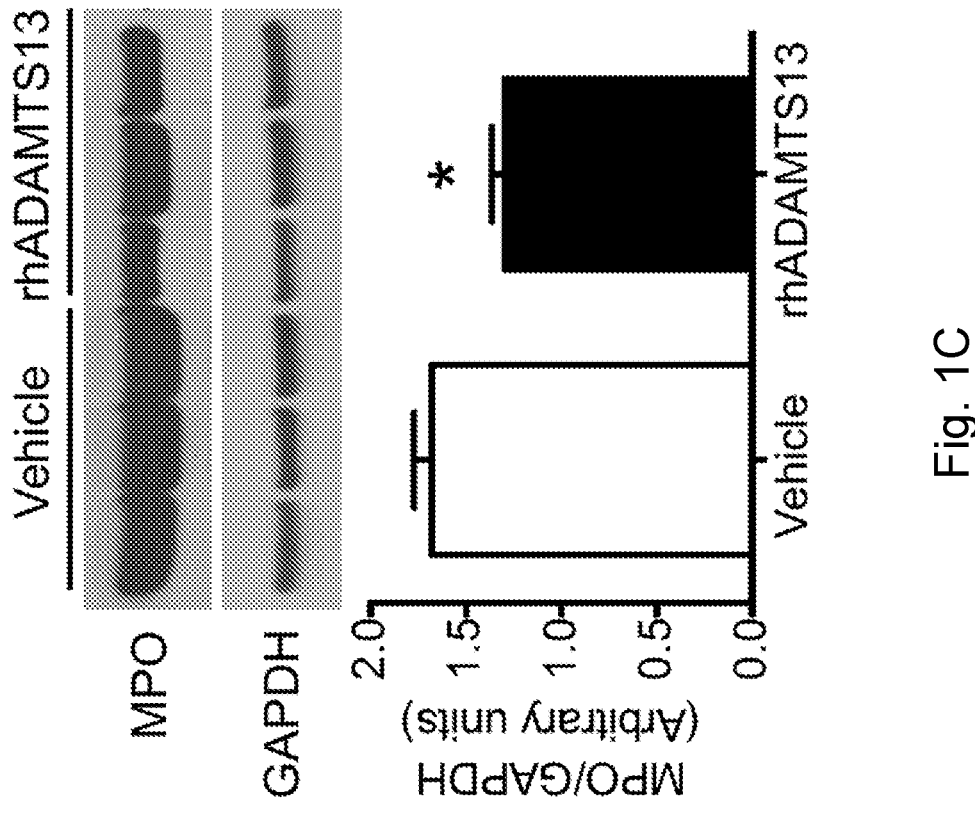
Figure 1E:
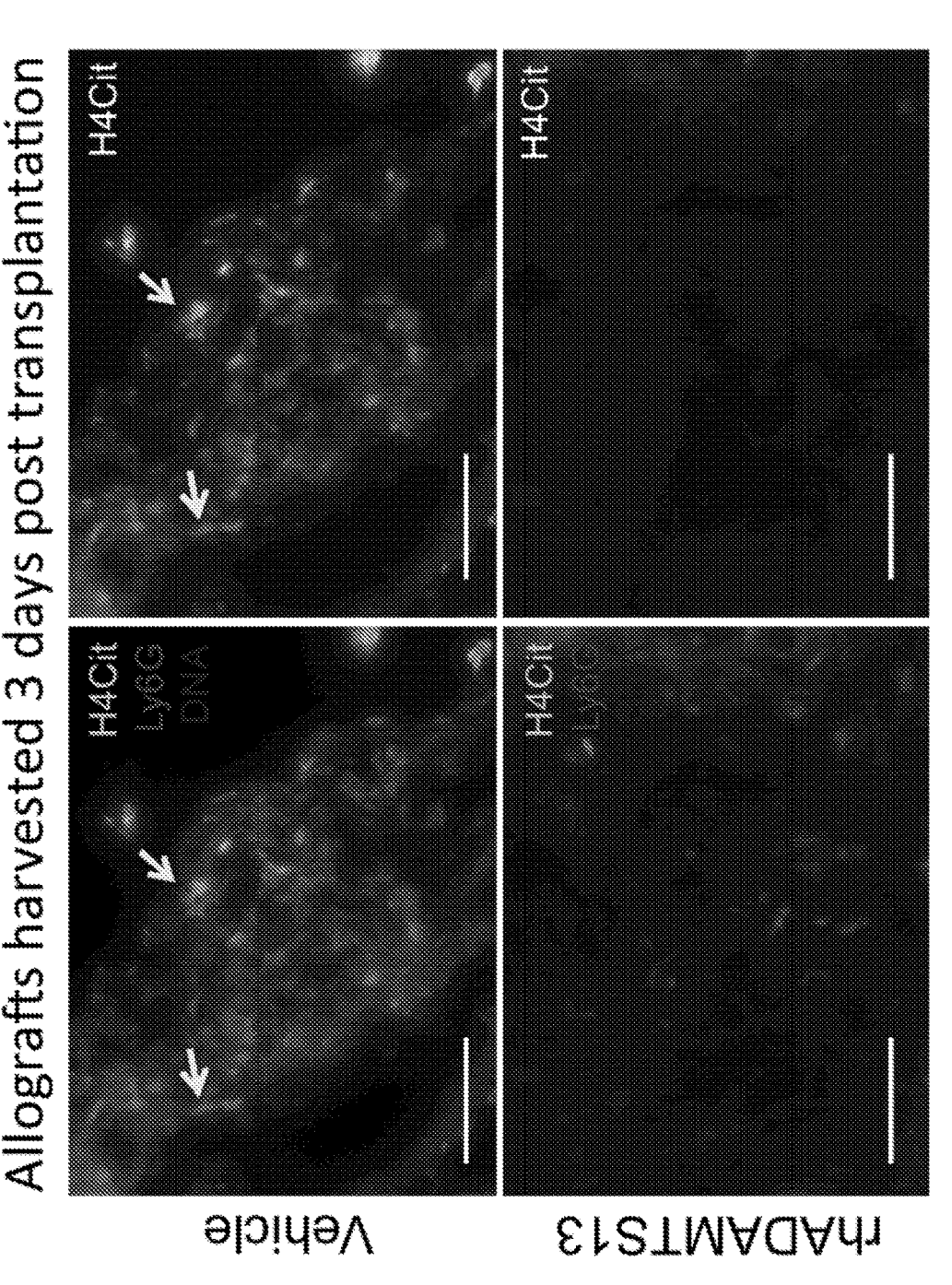

Western blot analysis showed that neutrophils (using MPO as the marker) and NETs (indicated by H4Cit) were present in the allografts of vehicle-treated mice 3 days post transplantation (see e.g., FIGS. 1C, 1D). RhADAMTS13 reduced neutrophil infiltration into the allografts by 23% (see e.g., FIG. 1C); however remarkably, NETs were undetectable in these allografts of the rhADAMTS13-treated mice (see e.g., FIG. 1D). Immunofluorescence microscopy revealed H4Cit+ extracellular DNA in areas with neutrophil accumulation (Ly6G+ areas, membrane marker of neutrophils) (see e.g., FIG. 1E, arrows). In contrast, there were fewer neutrophils and an absence of H4Cit+ cells in the allografts of rhADAMTS13-treated mice (see e.g., FIG. 1E), substantiating the findings of Western blotting (see e.g., FIGS. 1C, 1D). Thus, rhADAMTS13 decreases inflammation/prothrombotic potential in the allografts by reducing neutrophil content and NET burden.

2.3 NETs are Present in Human Skin Allografts

Figure 2B:
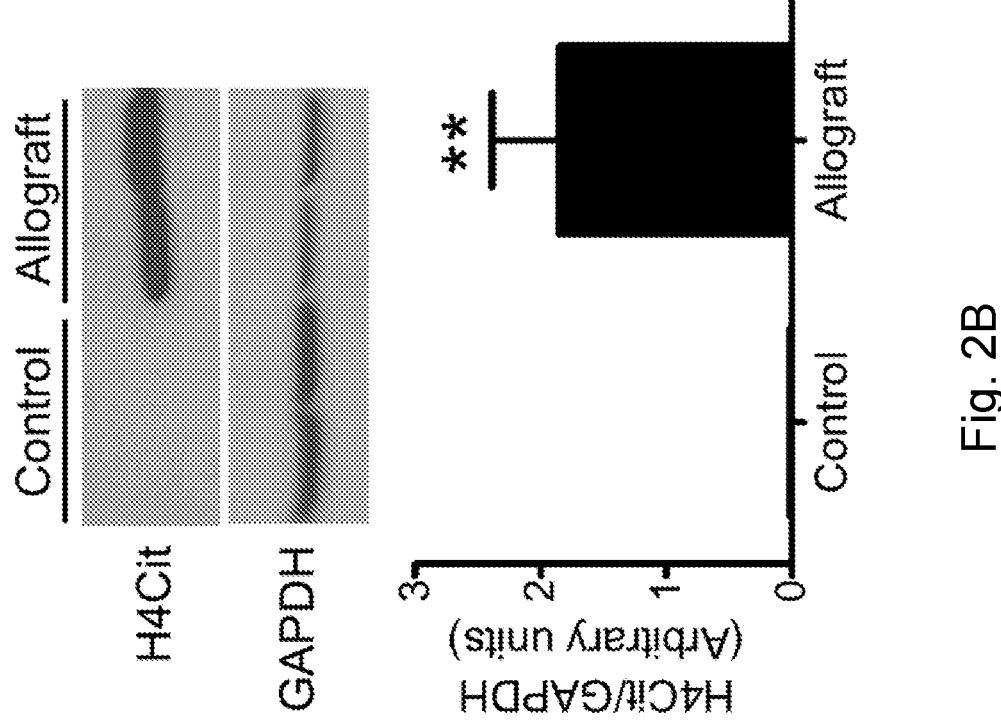
FIGS. 2A-2F shows the survival rate of allografts.
Figure 2A:
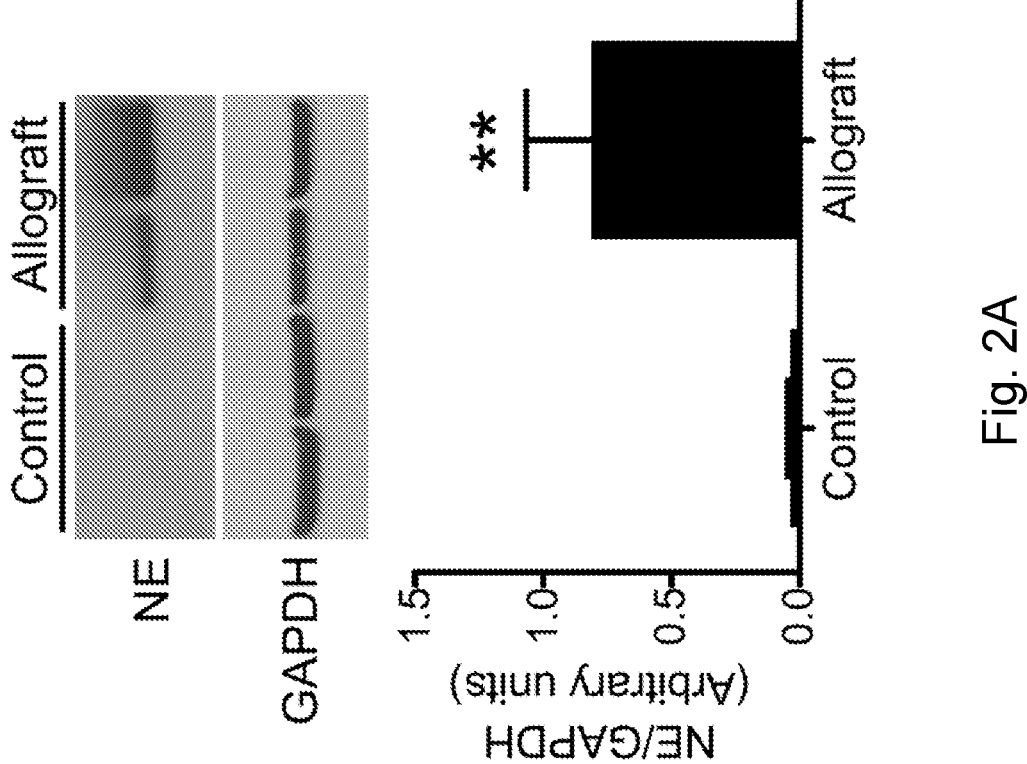
Figure 2D:
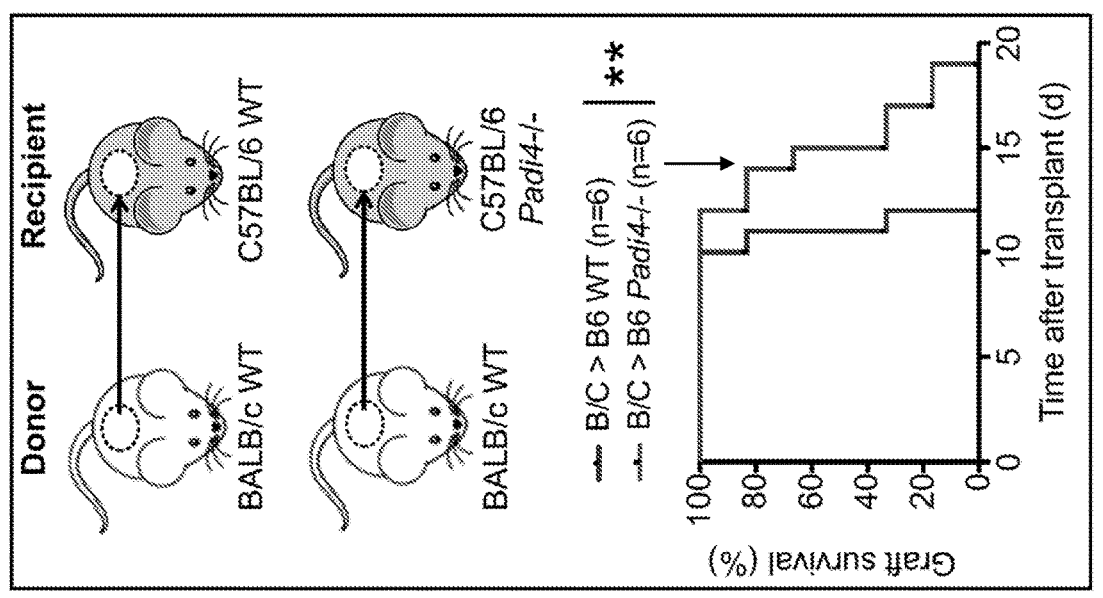
Figure 2C:
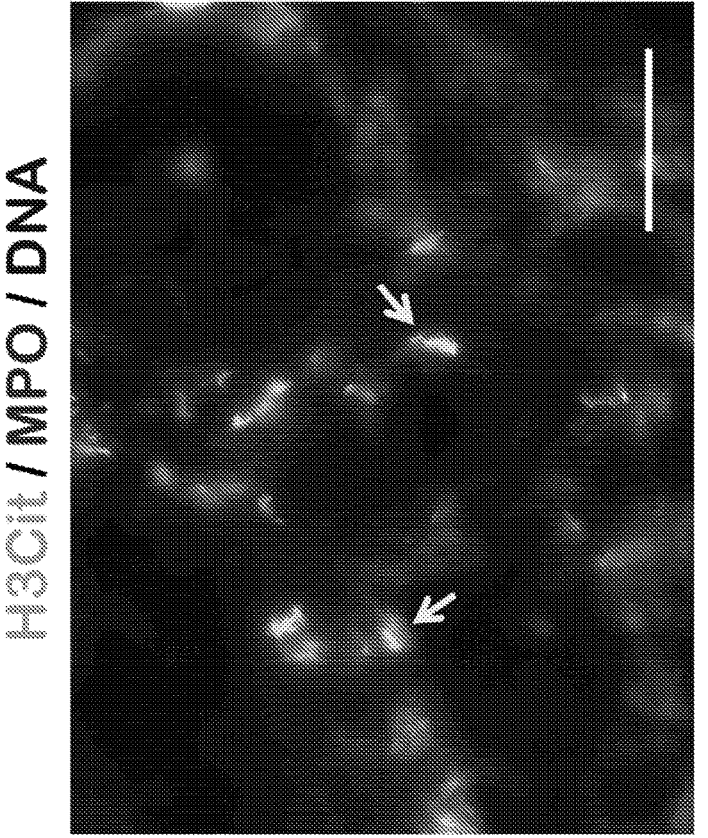

To evaluate whether the mouse findings are relevant to humans, NET presence in human skin allografts was examined. Western blot of surgically removed specimens showed that neutrophils (indicated by neutrophil elastase, NE) and NETs (indicated by H4Cit) were non-detectable in the control skin, while there were high levels of both in the allografts of the burn patients (see e.g., FIGS. 2A, 2B). Immunofluorescence staining showed that NETs (H3Cit+ and MPO+ extracellular DNA) were indeed present in these human allografts (see e.g., FIG. 2C), corroborating the observations of the mouse study.

2.4 PAD4 Deficiency and NET Cleavage Prolong Allograft Longevity

As rhADAMTS13 enhanced allograft longevity and reduced allograft NET burden, it was next asked whether inhibition of NET production offers benefits to the graft. The dorsal skin of BALB/c mice was transplanted to C57BL/6J WT and C57BL/6J Padi4−/− mice. Complete graft rejection occurred significantly later in Padi4−/− recipients. The median allograft survivals of WT and Padi4−/− recipients were 11 and 15 days, respectively (see e.g., FIG. 2D). The 36% increase in median survival indicates that absence of PAD4 is highly beneficial to allograft longevity. Although there was no apparent impact on allograft survival compared to vehicle-treatment when the Padi4−/− allograft recipients were administered with rhADAMTS13 (median survival of vehicle and rhADAMTS13-treated Padi4−/− were both 13 days in this experiment) (see e.g., FIG. 2E), the length or dosing with rhADAMTS13 may need to be adjusted or perhaps an effect would be seen with a reduction in PAD4 activation rather than a complete absence in PAD4 presence.

Figure 2F:
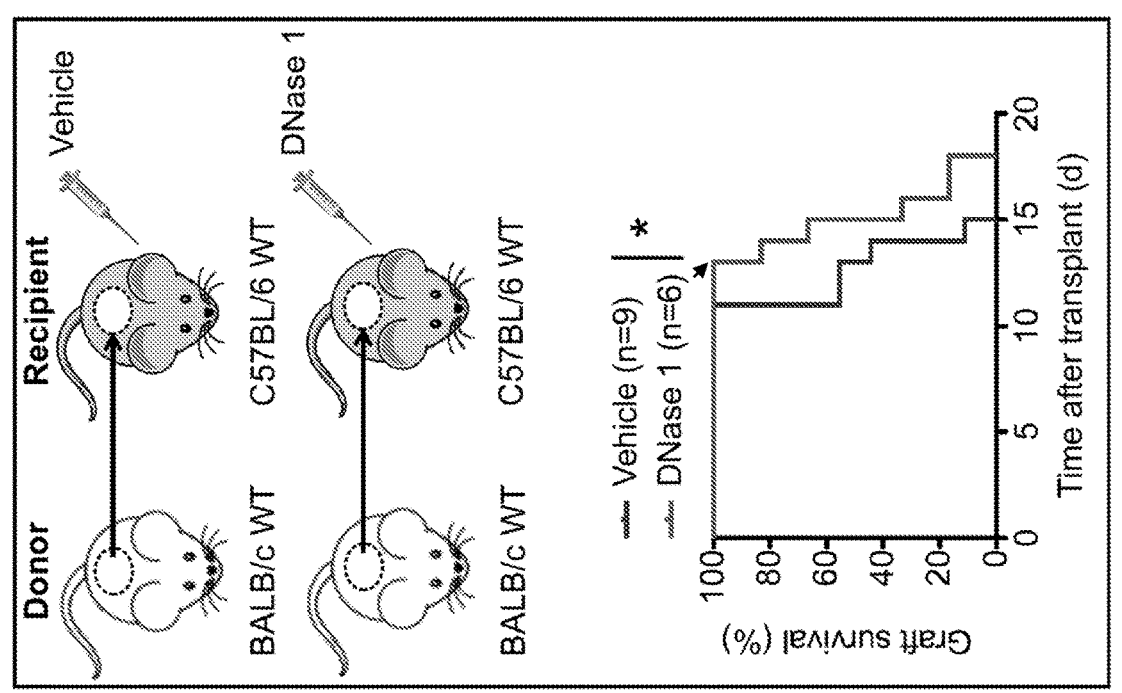
Figure 2E:
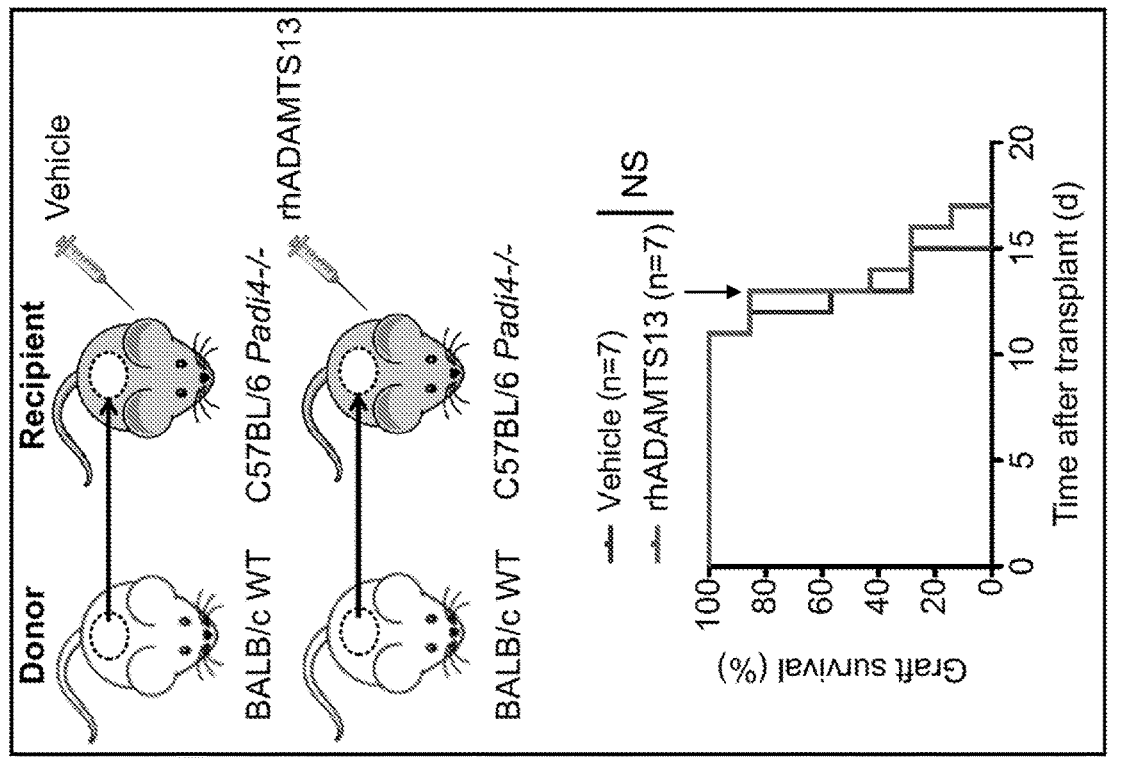

As DNase 1 cleaves the DNA backbone of NETs, 7-day DNase 1 treatment was also tested to determine whether it could increase allograft longevity (see e.g., FIG. 2F). The median allograft survival of vehicle- and DNase 1-treated mice were 13 and 15 days, respectively. Comparing to complete NET inhibition, DNase 1 treatment offered a 15% enhancement in median survival of the allografts.

3. Discussion

Plasma enzymes that cleave UL-VWF (ADAMTS13) and NETs (DNase 1) have been used clinically, but their therapeutic potential, as well as the role of UL-VWF and NETs, has not been explored in allogeneic skin transplant. The current study combined preclinical animal studies for drug testing, and burn patient specimen analysis to evaluate whether NETs can serve as a biomarker that indicates early skin allograft rejection. Administration of exogenous rhAD-AMTS13 or DNase 1 enhanced skin allograft longevity in mice; and importantly, inhibition of NET formation by knocking out PAD4 in the allograft recipient mice also markedly delayed allograft rejection. NET production in skin allografts was not confined to the mouse models, as a profound increase in the levels of neutrophils and NET biomarker (H3Cit and H4Cit) was also observed in the allografts of burn patients. In wild-type allograft mouse recipients, NETs were detectable 3 days post allograft transplant, where no signs of rejection can be observed macroscopically. In mice treated with rhADAMTS13, NETs were rare and grafts had a longer half-life. Thus, early emergence of NETs in the skin allograft may be an indicator of later graft rejection.

Neutrophils are the main leukocytes that are rapidly recruited to the wounds upon injury, and have been implicated in delayed wound healing (see e.g., Wong et al., Nat Med. 2015, 21(7):815-819). The current study showed for the first time that NETs are generated in skin allografts in both mice and humans, and contribute to allograft rejection. rhADAMTS13, which effectively dampens inflammatory responses post skin allograft transplant, profoundly enhanced allograft longevity as well. The exact mechanism through which rhADAMTS13 has this effect is not known, but the data described herein implicates the disruption of NET retention. Alternatively, NET formation could be reduced in the absence of neutrophil adhesion to UL-VWF.

Combined treatment of IL-2 and rapamycin was shown to maintain skin allograft survival for at least 60 days, however, the success is restricted to mouse strains with genetic backgrounds that differ only in minor histocompatibility antigens. This treatment has no beneficial effect when the donor and recipient are completely mismatched, such as C57BL/6 and BALB/c in the current setting described herein. This example shows that anti-UL-VWF and anti-NET treatments are more effective in enhancing skin allograft survival and open new avenues to delay allograft rejection. How exactly NETosis modulates alloimmune responses warrants further investigation. Proliferation and pro-inflammatory response of CD8+ T cells mediate skin allograft rejection after burn injuries in mice. As NETting neutrophils can prime T cells for proliferation and cytokine production, it is possible that NETs contribute to the development of alloimmune responses via T cell activation.

In summary, rhADAMTS13 lessens inflammation in allografts by reducing NET burden, resulting in enhanced allograft survival. RhADAMTS13 and anti-NET treatments are new therapeutic strategies to promote skin allograft longevity and hence the survival of patients (e.g., patients with severe burns).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents, applications, publications, test methods, literature, and other materials cited herein are hereby incorporated by reference in their entirety as if physically present in this specification. All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

REFERENCES

1. Kitala D, Kawecki M, Klama-Baryla A, et al. Allogeneic vs. Autologous Skin Grafts in the Therapy of Patients with Burn Injuries: A Retrospective, Open-label Clinical Study with Pair Matching. Adv Clin Exp Med. 2016; 25(5):923-929.

2. Landsman A, Rosines E, Houck A, et al. Characterization of a Cryopreserved Split-Thickness Human Skin Allograft-TheraSkin. Adv Skin Wound Care. 2016; 29(9): 399-406.

3. Johnson B W, Madson A Q, Bong-Thakur S, et al. Combat-related facial burns: analysis of strategic pitfalls. J Oral Maxillofac Surg. 2015; 73(1):106-111.

4. Wolf S E, Kauvar D S, Wade C E, et al. Comparison between civilian burns and combat burns from Operation Iraqi Freedom and Operation Enduring Freedom. Ann Surg. 2006; 243(6):786-792; discussion 792-785.

5. Benichou G, Yamada Y, Yun S H, et al. Immune recognition and rejection of allogeneic skin grafts. Immunotherapy. 2011; 3(6):757-770.

6. Kanitakis J, Petruzzo P, Gazarian A, et al. Capillary Thrombosis in the Skin: A Pathologic Hallmark of Severe/Chronic Rejection of Human Vascularized Composite Tissue Allografts?Transplantation. 2016; 100(4):954-957.

7. Chen J, Chung D W. Inflammation, von Willebrand factor, and ADAMTS13. Blood. 2018; 132(2):141-147.

8. Kawecki C, Lenting P J, Denis C V. von Willebrand factor and inflammation. J Thromb Haemost. 2017; 15(7):1285-1294.

9. Ko S, Okano E, Kanehiro H, et al. Plasma ADAMTS13 activity may predict early adverse events in living donor liver transplantation: observations in 3 cases. Liver Transpl. 2006; 12(5):859-869.

10. Kiuchi T, Oldhafer K J, Schlitt H J, et al. Background and prognostic implications of perireperfusion tissue injuries in human liver transplants: a panel histochemical study. Transplantation. 1998; 66(6):737-747.

11. Chauhan A K, Kisucka J, Brill A, et al. ADAMTS13: a new link between thrombosis and inflammation. J Exp Med. 2008; 205(9):2065-2074.

12. Fuchs T A, Brill A, Duerschmied D, et al. Extracellular DNA traps promote thrombosis. Proc Natl Acad Sci USA. 2010; 107(36):15880-15885.

13. Grassle S, Huck V, Pappelbaum K I, et al. von Willebrand factor directly interacts with DNA from neutrophil extracellular traps. Arterioscler Thromb Vase Biol. 2014; 34(7):1382-1389.

14. Lewis H D, Liddle J, Coote J E, et al. Inhibition of PAD4 activity is sufficient to disrupt mouse and human NET formation. Nat Chem Biol. 2015; 11(3):189-191.

15. Li P, Li M, Lindberg M R, et al. PAD4 is essential for antibacterial innate immunity mediated by neutrophil extracellular traps. J Exp Med. 2010; 207(9):1853-1862.

16. Saffarzadeh M, Juenemann C, Queisser M A, et al. Neutrophil extracellular traps directly induce epithelial and endothelial cell death: a predominant role of histones. PLoS One. 2012; 7(2):e32366.

17. Xu J, Zhang X, Pelayo R, et al. Extracellular histones are major mediators of death in sepsis. Nat Med. 2009; 15(11):1318-1321.

18. Wong S L, Demers M, Martinod K, et al. Diabetes primes neutrophils to undergo NETosis, which impairs wound healing. Nat Med. 2015; 21(7):815-819.

19. Sayah D M, Mallavia B, Liu F, et al. Neutrophil extracellular traps are pathogenic in primary graft dysfunction after lung transplantation. Am J Respir Crit Care Med. 2015; 191(4):455-463.

20. Scozzi D, Wang X, Liao F, et al. Neutrophil extracellular trap fragments stimulate innate immune responses that prevent lung transplant tolerance. Am J Transplant. 2019; 19(4):1011-1023.

21. Cheng C H, Lee C F, Fryer M, et al. Murine Full-thickness Skin Transplantation. J Vis Exp. 2017(119).

22. Scully M, Knobl P, Kentouche K, et al. Recombinant ADAMTS-13: first-in-human pharmacokinetics and safety in congenital thrombotic thrombocytopenic purpura. Blood. 2017; 130(19):2055-2063.

23. Suri R. The use of human deoxyribonuclease (rhDNase) in the management of cystic fibrosis. Biodrugs. 2005; 19(3):135-144.

24. Pilon C B, Petillon S, Naserian S, et al. Administration of low doses of IL-2 combined to rapamycin promotes allogeneic skin graft survival in mice. Am J Transplant. 2014; 14(12):2874-2882.

25. Maile R, Barnes C M, Nielsen A I, et al. Lymphopenia-induced homeostatic proliferation of CD8+ T cells is a mechanism for effective allogeneic skin graft rejection following burn injury. J Immunol. 2006; 176(11):6717-6726.

26. Tillack K, Breiden P, Martin R, et al. T lymphocyte priming by neutrophil extracellular traps links innate and adaptive immune responses. J Immunol. 2012; 188(7): 3150-3159.

27. Gelman A E, Li W, Richardson S B, et al. Cutting edge: Acute lung allograft rejection is independent of secondary lymphoid organs. J Immunol. 2009; 182(7):3969-3973.

28. Sun B, Dwivedi N, Bechtel T J, et al. Citrullination of NF-kappaB p65 promotes its nuclear localization and TLR-induced expression of IL-1beta and TNFalpha. Sci Immunol. 2017; 2(12).

29. Mishra N, Schwerdtner L, Sams K, et al. Cutting Edge: Protein Arginine Deiminase 2 and 4 Regulate NLRP3 Inflammasome-Dependent IL-1beta Maturation and ASC Speck Formation in Macrophages. J Immunol. 2019; 203(4):795-800.

30. Münzer P, Negro R, Magupalli V, et al. Abstract 118: Assembly of the Nlrp3 inflammasome regulates NET formation and is promoted by the vimentin intermediate filament cytoskeletal system. Arterioscler Thromb Vase Biol. 2019; 39:A118.

31. Otawara M, Roushan M, Wang X, et al. Microfluidic Assay Measures Increased Neutrophil Extracellular Traps Circulating in Blood after Burn Injuries. Sci Rep. 2018; 8(1):16983.

32. Oztirk M A, Babacanlar N, Akkoz C, et al. Can burn injury cause thrombotic thrombocytopenic purpura?South Clin Ist Euras. 2019; 30(2):175-177.

33. Emil S, Rockstad R, Vannix D. Hemolytic uremic syndrome in a child with burn injuries. J Burn Care Rehabil. 1998; 19(2):135-137.

34. Moake J L. Thrombotic microangiopathies. N Engl J Med. 2002; 347(8):589-600.

35. Nolasco L H, Turner N A, Bernardo A, et al. Hemolytic uremic syndrome-associated Shiga toxins promote endothelial-cell secretion and impair ADAMTS13 cleavage of unusually large von Willebrand factor multimers. Blood. 2005; 106(13):4199-4209.

36. Sorvillo N, Mizurini D M, Coxon C, et al. Plasma Peptidylarginine Deiminase IV Promotes VWF-Platelet String Formation and Accelerates Thrombosis After Vessel Injury. Circ Res. 2019; 125(5):507-519.

What is claimed is:

1. A method for treating or preventing graft rejection in a subject that received a skin graft, the method comprising administering to the subject in need thereof a therapeutically effective amount of a composition comprising A Disintegrin And Metalloproteinase with Thrombospondin type 1 motif, member-13 (ADAMTS13), wherein administering ADAMTS13 reduces and/or prevents neutrophil extracellular trap (NET) burden in the skin graft.

2. The method of claim 1, wherein the subject is administered ADAMTS13 after at least one symptom of graft rejection is present, or wherein the subject is administered ADAMTS13 before a symptom of graft rejection is present.

3. The method of claim 1, wherein administering ADAMTS13 reduces and/or prevents at least one of graft deterioration, graft desiccation, graft shrinkage, scab formation, graft hardening, loss of hair, graft dysfunction, organ deterioration, organ damage, organ dysfunction, cell damage, inflammation, swelling, erythema, seroma, severity of pain, infection, neutrophil recruitment, lymphocyte recruitment, platelet aggregation, microthrombosis, generation of angiogenesis or a combination of any thereof as compared to control, the subject without treatment, and/or the subject before transplantation.

4. The method of claim 3, wherein the lymphocyte recruitment is T-cell recruitment.

5. The claim of claim 3, wherein the level of NET burden is determined by measuring the level of histone modifications, cell-free DNA, citrullinated histone H3 (H3Cit), citrullinated histone H4 (H4Cit), neutrophil elastase (NE), and/or myeloperoxidase (MPO) DNA conjugates.

6. The method of claim 1, wherein administering ADAMTS13 results in at least one of increased survival of the graft, improved organ function, increased survival of the subject, or a combination of any thereof as compared to control, the subject without treatment, and/or the subject before transplantation.

7. The method of claim 1, wherein the therapeutically effective amount of ADAMTS13 is from about 20 to about 6,000 international units per kilogram body weight.

8. The method of claim 1, wherein the composition comprising ADAMTS13 is administered in a single bolus injection, monthly, every two weeks, weekly, twice a week, daily, every twelve hours, every eight hours, every six hours, every four hours, or every two hours, and wherein the composition comprising ADAMTS13 is administered intravenously, subcutaneously, or dermally.

9. The method of claim 1, wherein the ADAMTS13 is recombinant ADAMTS13, or wherein the ADAMTS13 is plasma derived.

10. The method of claim 1, wherein the subject is a mammal or wherein the subject is a human.

11. The method of claim 1, wherein the composition is in a stable aqueous solution ready for administration.

12. The method of claim 1, wherein the therapeutically effective amount of the composition comprising ADAMTS13: is administered to the subject within 48 hours after receiving the graft, or is sufficient to maintain an effective level of ADAMTS13 activity in the subject.

13. The method of claim 1, wherein the graft is an allograft; an autograft; a xenograft obtained from a pig, a primate, or a cow; an artificially manufactured device; or wherein the graft is transplanted to the subject that is suffering from a wound, a burn, a damaged organ, or an infection, and/or the subject has undergone surgery.

14. The method of claim 1, further comprising modifying one or more additional genes or gene products such that the expression and/or function of said additional gene(s) or gene product(s) is reduced or eliminated, wherein said additional gene(s) or gene product(s) are PAD4, H3Cit, H4Cit, MPO, NE, or NLRP3.

15. The method of claim 14, wherein the modifying of one or more additional genes comprises: disrupting said gene(s) with a site-specific nuclease; administering an RNA interference (RNAi) molecule or an antisense oligonucleotide; or administering one or more of a small molecule inhibitor, a peptide, an antibody or antibody fragment, and an aptamer.

16. The method of claim 15, wherein the site-specific nuclease comprises a Cas protein and a guide RNA, a zinc finger nuclease (ZFN), a TALEN nuclease, or a mega-TALEN nuclease; or wherein the RNAi molecule is a small interfering RNA (siRNA) or a small hairpin RNA (shRNA).

17. The method of claim 1, further comprising inhibiting NET formation and/or neutrophil infiltration.

18. The method of claim 17, wherein the inhibiting NET formation comprises: administering one or more of a small molecule inhibitor, a peptide, an antibody or antibody fragment, and an aptamer; or by administering, increasing the expression of, and/or activating DNase 1.

* * * * *